US006020477A

United States Patent [19]

Diu et al.

[11] Patent Number: 6,020,477

[45] Date of Patent: *Feb. 1, 2000

[54] DNA SEQUENCES CODING FOR THE HUMAN PROTEINS TX AND TY RELATED TO THE INTERLEUKIN-1β CONVERTING ENZYME

[75] Inventors: Anita Diu, Charenton-le-Pont; Chi Faucheu, Emervainville; Thierry Hercend, Charenton-le-Pont; Jean Louis Lalanne, Fontenay-sous-Bois, all of France; David J Livingston; Michael Su, both of Newton, Mass.

[73] Assignee: Hoechst Marion Roussel, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,900

[22] PCT Filed: Aug. 1, 1995

[86] PCT No.: PCT/FR95/01035

§ 371 Date: Apr. 30, 1997

§ 102(e) Date: Apr. 30, 1997

[87] PCT Pub. No.: WO96/04387

PCT Pub. Date: Feb. 15, 1996

[30] Foreign Application Priority Data

Aug. 2, 1994 [FR] France .................................. 94/09567

[51] Int. Cl.[7] .......................... C07H 21/04; C12N 15/63; C12N 15/00

[52] U.S. Cl. ....................... 536/23.5; 435/69.1; 435/71.1; 435/320.1; 435/455

[58] Field of Search ............................... 435/71.1, 320.1, 435/69.1, 455; 536/23.5

[56] References Cited

U.S. PATENT DOCUMENTS 5,552,536 9/1996 Nicholson et al. .

OTHER PUBLICATIONS

Alnemii et al. Cell 87:171, 1996.

Watson et al Molecular Biology of the Gene Bensamin Cummings Pub. Co. Inc. Menlo Park California 1987 pp. 88–89.

*Primary Examiner*—Thomas M. Cunningham
*Assistant Examiner*—Martha T. Lubet
*Attorney, Agent, or Firm*—Bierman, Muserlian and Lucas

[57] ABSTRACT

An isolated DNA molecule consisting of SEQ I.D. No: 22 encoding a polypeptide having a protease activity and capable of inducing a apoptosis and the method of producing a polypeptide consisting of the said sequence.

2 Claims, 11 Drawing Sheets

```
            *         *         *         *         *         *
  1 GAAATGACTACAGAGCTGGAGGCATTTGCTCACCGCCCAGAGCACAAGACCTCTGACAGC  60

            *         *         *         *         *         *
 61 ACCTTCCCGGTGTTCTTGTCTCATGGTGTTCGGGAAGGCATTTGTGGGAAGAAATACTCT 120

            *         *         *         *         *         *
121 GAACAAGTCCCTGATATATTACAATTCAATGAAATATTTAAAATGTTGAATAGCAAGAAC 180

            *         *         *         *         *
181 TGCCCAAGTTTGAAGGACAAACCCAAGGTGATCATCTTCGAGGCCTGCTGTGGTG      235
```

FIG. 2

```
GCTCTTTCCA ACGCTGTAAA AAAGGACAGA GGCTGTTCCC T ATG GCA GAA GGC      53
                                              Met Ala Glu Gly
                                               1

AAC CAC AGA AAA AAG CCA CTT AAG GTG TTG GAA TCC CTG GGC AAA GAT   101
Asn His Arg Lys Lys Pro Leu Lys Val Leu Glu Ser Leu Gly Lys Asp
 5                  10                  15                  20

TTC CTC ACT GGT GTT TTG GAT AAC TTG GTG GAA CAA AAT GTA CTG AAC   149
Phe Leu Thr Gly Val Leu Asp Asn Leu Val Glu Gln Asn Val Leu Asn
                25                  30                  35

TGG AAG GAA GAG GAA AAA AAG AAA TAT TAC GAT GCT AAA ACT GAA GAC   197
Trp Lys Glu Glu Glu Lys Lys Lys Tyr Tyr Asp Ala Lys Thr Glu Asp
            40                  45                  50

AAA GTT CGG GTC ATG GCA GAC TCT ATG CAA GAG AAG CAA CGT ATG GCA   245
Lys Val Arg Val Met Ala Asp Ser Met Gln Glu Lys Gln Arg Met Ala
        55                  60                  65

GGA CAA ATG CTT CTT CAA ACC TTT TTT AAC ATA GAC CAA ATA TCC CCC   293
Gly Gln Met Leu Leu Gln Thr Phe Phe Asn Ile Asp Gln Ile Ser Pro
    70                  75                  80

AAT AAA AAA GCT CAT CCG AAT ATG GAG GCT GGA CCA CCT GAG TCA GGA   341
Asn Lys Lys Ala His Pro Asn Met Glu Ala Gly Pro Pro Glu Ser Gly
 85                 90                  95                  100

GAA TCT ACA GAT GCC CTC AAG CTT TGT CCT CAT GAA GAA TTC CTG AGA   389
Glu Ser Thr Asp Ala Leu Lys Leu Cys Pro His Glu Glu Phe Leu Arg
                105                 110                 115

CTA TGT AAA GAA AGA GCT GAA GAG ATC TAT CCA ATA AAG GAG AGA AAC   437
Leu Cys Lys Glu Arg Ala Glu Glu Ile Tyr Pro Ile Lys Glu Arg Asn
            120                 125                 130

AAC CGC ACA CGC CTG GCT CTC ATC ATA TGC AAT ACA GAG TTT GAC CAT   485
Asn Arg Thr Arg Leu Ala Leu Ile Ile Cys Asn Thr Glu Phe Asp His
        135                 140                 145

CTG CCT CCG AGG AAT GGA GCT GAC TTT GAC ATC ACA GGG ATG AAG GAG   533
Leu Pro Pro Arg Asn Gly Ala Asp Phe Asp Ile Thr Gly Met Lys Glu
    150                 155                 160
```

FIG. 3A

```
CTA CTT GAG GGT CTG GAC TAT AGT GTA GAT GTA GAA GAG AAT CTG ACA    581
Leu Leu Glu Gly Leu Asp Tyr Ser Val Asp Val Glu Glu Asn Leu Thr
165                 170                 175                 180

GCC AGG GAT ATG GAG TCA GCG CTG AGG GCA TTT GCT ACC AGA CCA GAG    629
Ala Arg Asp Met Glu Ser Ala Leu Arg Ala Phe Ala Thr Arg Pro Glu
                185                 190                 195

CAC AAG TCC TCT GAC AGC ACA TTC TTG GTA CTC ATG TCT CAT GGC ATC    677
His Lys Ser Ser Asp Ser Thr Phe Leu Val Leu Met Ser His Gly Ile
            200                 205                 210

CTG GAG GGA ATC TGC GGA ACT GTG CAT GAT GAG AAA AAA CCA GAT GTG    725
Leu Glu Gly Ile Cys Gly Thr Val His Asp Glu Lys Lys Pro Asp Val
        215                 220                 225

CTG CTT TAT GAC ACC ATC TTC CAG ATA TTC AAC AAC CGC AAC TGC CTC    773
Leu Leu Tyr Asp Thr Ile Phe Gln Ile Phe Asn Asn Arg Asn Cys Leu
    230                 235                 240

AGT CTG AAG GAC AAA CCC AAG GTC ATC ATT GTC CAG GCC TGC AGA GGT    821
Ser Leu Lys Asp Lys Pro Lys Val Ile Ile Val Gln Ala Cys Arg Gly
245                 250                 255                 260

GCA AAC CGT GGG GAA CTG TGG GTC AGA GAC TCT CCA GCA TCC TTG GAA    869
Ala Asn Arg Gly Glu Leu Trp Val Arg Asp Ser Pro Ala Ser Leu Glu
                265                 270                 275

GTG GCC TCT TCA CAG TCA TCT GAG AAC CTG GAG GAA GAT GCT GTT TAC    917
Val Ala Ser Ser Gln Ser Ser Glu Asn Leu Glu Glu Asp Ala Val Tyr
            280                 285                 290

AAG ACC CAC GTG GAG AAG GAC TTC ATT GCT TTC TGC TCT TCA ACG CCA    965
Lys Thr His Val Glu Lys Asp Phe Ile Ala Phe Cys Ser Ser Thr Pro
        295                 300                 305

CAC AAC GTG TCC TGG AGA GAC AGC ACA ATG GGC TCT ATC TTC ATC ACA   1013
His Asn Val Ser Trp Arg Asp Ser Thr Met Gly Ser Ile Phe Ile Thr
    310                 315                 320

CAA CTC ATC ACA TGC TTC CAG AAA TAT TCT TGG TGC TGC CAC CTA GAG   1061
Gln Leu Ile Thr Cys Phe Gln Lys Tyr Ser Trp Cys Cys His Leu Glu
325                 330                 335                 340
```

FIG. 3B

```
GAA GTA TTT CGG AAG GTA CAG CAA TCA TTT GAA ACT CCA AGG GCC AAA  1109
Glu Val Phe Arg Lys Val Gln Gln Ser Phe Glu Thr Pro Arg Ala Lys
                345                 350                 355

GCT CAA ATG CCC ACC ATA GAA CGA CTG TCC ATG ACA AGA TAT TTC TAC  1157
Ala Gln Met Pro Thr Ile Glu Arg Leu Ser Met Thr Arg Tyr Phe Tyr
            360                 365                 370

CTC TTT CCT GGC AAT TGAAAATGGA AGCCACAAGC AGCCCAGCCC TCCTTAATCA  1212
Leu Phe Pro Gly Asn
        375

ACTTCAAGGA GCACCTTCAT TAGTACAGCT TGCATATTTA ACATTTTGTA TTTCAATAAA 1272

AGTGAAGACA AAAAAAAAA                                              1291
```

FIG. 3C

SEQUENCE LISTING

```
(1) GENERAL INFORMATION:

   (iii) NUMBER OF SEQUENCES: 42


(2) INFORMATION FOR SEQ ID NO: 1:

     (i) SEQUENCE CHARACTERISTICS:
          (A) LENGTH: 1291
          (B) TYPE: nucleic acid
```

```
        (C) STRANDEDNESS: single
        (D) TOPOLOGY: linear

   (ii) MOLECULE TYPE: cDNA

   (vi) ORIGINAL SOURCE:
        (A) ORGANISM: Homo sapiens

   (ix) FEATURE:
        (A) NAME/KEY: CDS

   (xi) SEQUENCE DESCRIPTION: SEQ ID NO: 1:

GCTCTTTCCA ACGCTGTAAA AAAGGACAGA GCTGTTCCC T ATG GCA GAA GGC         53
                                             Met Ala Glu Gly
                                               1

AAC CAC AGA AAA AAG CCA CTT AAG GTG TTG GAA TCC CTG GGC AAA GAT     101
Asn His Arg Lys Lys Pro Leu Lys Val Leu Glu Ser Leu Gly Lys Asp
  5                  10                  15                  20

TTC CTC ACT GGT GTT TTG GAT AAC TTG GTG GAA CAA AAT GTA CTG AAC     149
Phe Leu Thr Gly Val Leu Asp Asn Leu Val Glu Gln Asn Val Leu Asn
                 25                  30                  35

TGG AAG GAA GAG GAA AAA AAG AAA TAT TAC GAT GCT AAA ACT GAA GAC     197
Trp Lys Glu Glu Glu Lys Lys Lys Tyr Tyr Asp Ala Lys Thr Glu Asp
             40                  45                  50

AAA GTT CGG GTC ATG GCA GAC TCT ATG CAA GAG AAG CAA CGT ATG GCA     245
Lys Val Arg Val Met Ala Asp Ser Met Gln Glu Lys Gln Arg Met Ala
         55                  60                  65

GGA CAA ATG CTT CTT CAA ACC TTT TTT AAC ATA GAC CAA ATA TCC CCC     293
Gly Gln Met Leu Leu Gln Thr Phe Phe Asn Ile Asp Gln Ile Ser Pro
     70                  75                  80

AAT AAA AAA GCT CAT CCG AAT ATG GAG GCT GGA CCA CCT GAG TCA GGA     341
Asn Lys Lys Ala His Pro Asn Met Glu Ala Gly Pro Pro Glu Ser Gly
 85                  90                  95                 100

GAA TCT ACA GAT GCC CTC AAG CTT TGT CCT CAT GAA GAA TTC CTG AGA     389
Glu Ser Thr Asp Ala Leu Lys Leu Cys Pro His Glu Glu Phe Leu Arg
                105                 110                 115

CTA TGT AAA GAA AGA GCT GAA GAG ATC TAT CCA ATA AAG GAG AGA AAC     437
Leu Cys Lys Glu Arg Ala Glu Glu Ile Tyr Pro Ile Lys Glu Arg Asn
            120                 125                 130

AAC CGC ACA CGC CTG GCT CTC ATC ATA TGC AAT ACA GAG TTT GAC CAT     485
Asn Arg Thr Arg Leu Ala Leu Ile Ile Cys Asn Thr Glu Phe Asp His
        135                 140                 145

CTG CCT CCG AGG AAT GGA GCT GAC TTT GAC ATC ACA GGG ATG AAG GAG     533
Leu Pro Pro Arg Asn Gly Ala Asp Phe Asp Ile Thr Gly Met Lys Glu
    150                 155                 160

CTA CTT GAG GGT CTG GAC TAT AGT GTA GAT GTA GAA GAG AAT CTG ACA     581
Leu Leu Glu Gly Leu Asp Tyr Ser Val Asp Val Glu Glu Asn Leu Thr
165                 170                 175                 180

GCC AGG GAT ATG GAG TCA GCG CTG AGG GCA TTT GCT ACC AGA CCA GAG     629
Ala Arg Asp Met Glu Ser Ala Leu Arg Ala Phe Ala Thr Arg Pro Glu
                185                 190                 195

CAC AAG TCC TCT GAC AGC ACA TTC TTG GTA CTC ATG TCT CAT GGC ATC     677
His Lys Ser Ser Asp Ser Thr Phe Leu Val Leu Met Ser His Gly Ile
            200                 205                 210

CTG GAG GGA ATC TGC GGA ACT GTG CAT GAT GAG AAA AAA CCA GAT GTG     725
Leu Glu Gly Ile Cys Gly Thr Val His Asp Glu Lys Lys Pro Asp Val
        215                 220                 225

CTG CTT TAT GAC ACC ATC TTC CAG ATA TTC AAC AAC CGC AAC TGC CTC     773
Leu Leu Tyr Asp Thr Ile Phe Gln Ile Phe Asn Asn Arg Asn Cys Leu
    230                 235                 240

AGT CTG AAG GAC AAA CCC AAG GTC ATC ATT GTC CAG GCC TGC AGA GGT     821
Ser Leu Lys Asp Lys Pro Lys Val Ile Ile Val Gln Ala Cys Arg Gly
245                 250                 255                 260
```

```
GCA AAC CGT GGG GAA CTG TGG GTC AGA GAC TCT CCA GCA TCC TTG GAA      869
Ala Asn Arg Gly Glu Leu Trp Val Arg Asp Ser Pro Ala Ser Leu Glu
                265                 270                 275

GTG GCC TCT TCA CAG TCA TCT GAG AAC CTG GAG GAA GAT GCT GTT TAC      917
Val Ala Ser Ser Gln Ser Ser Glu Asn Leu Glu Glu Asp Ala Val Tyr
            280                 285                 290

AAG ACC CAC GTG GAG AAG GAC TTC ATT GCT TTC TGC TCT TCA ACG CCA      965
Lys Thr His Val Glu Lys Asp Phe Ile Ala Phe Cys Ser Ser Thr Pro
        295                 300                 305

CAC AAC GTG TCC TGG AGA GAC AGC ACA ATG GGC TCT ATC TTC ATC ACA     1013
His Asn Val Ser Trp Arg Asp Ser Thr Met Gly Ser Ile Phe Ile Thr
    310                 315                 320

CAA CTC ATC ACA TGC TTC CAG AAA TAT TCT TGG TGC TGC CAC CTA GAG     1061
Gln Leu Ile Thr Cys Phe Gln Lys Tyr Ser Trp Cys Cys His Leu Glu
325                 330                 335                 340

GAA GTA TTT CGG AAG GTA CAG CAA TCA TTT GAA ACT CCA AGG GCC AAA     1109
Glu Val Phe Arg Lys Val Gln Gln Ser Phe Glu Thr Pro Arg Ala Lys
                345                 350                 355

GCT CAA ATG CCC ACC ATA GAA CGA CTG TCC ATG ACA AGA TAT TTC TAC     1157
Ala Gln Met Pro Thr Ile Glu Arg Leu Ser Met Thr Arg Tyr Phe Tyr
            360                 365                 370

CTC TTT CCT GGC AAT TGAAAATGGA AGCCACAAGC AGCCCAGCCC TCCTTAATCA     1212
Leu Phe Pro Gly Asn
        375

ACTTCAAGGA GCACCTTCAT TAGTACAGCT TGCATATTTA ACATTTTGTA TTTCAATAAA   1272

AGTGAAGACA AAAAAAAAA                                                1291
```

(2) INFORMATION FOR SEQ ID NO: 2:

(i) SEQUENCE CHARACTERISTICS:
(A) LENGTH: 377
(B) TYPE: amino acid
(D) TOPOLOGY: linear (ii) MOLECULE TYPE: protein (xi) SEQUENCE DESCRIPTION: SEQ ID NO: 2:

```
Met Ala Glu Gly Asn His Arg Lys Lys Pro Leu Lys Val Leu Glu Ser
  1               5                  10                  15

Leu Gly Lys Asp Phe Leu Thr Gly Val Leu Asp Asn Leu Val Glu Gln
            20                  25                  30

Asn Val Leu Asn Trp Lys Glu Glu Glu Lys Lys Lys Tyr Tyr Asp Ala
        35                  40                  45

Lys Thr Glu Asp Lys Val Arg Val Met Ala Asp Ser Met Gln Glu Lys
     50                  55                  60

Gln Arg Met Ala Gly Gln Met Leu Leu Gln Thr Phe Phe Asn Ile Asp
 65                  70                  75                  80

Gln Ile Ser Pro Asn Lys Lys Ala His Pro Asn Met Glu Ala Gly Pro
                 85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
```

```
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
    210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375
```

(2) INFORMATION FOR SEQ ID NO: 3:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (x) PUBLICATION INFORMATION:
(A) AUTHORS: Thornberry, Nancy A.
Bull, Herbert G.
Calaycay, Jimmy R.
Chapman, Kevin T.
Howard, Andrew D.
Kostura, Matthew J.
Miller, Douglas K.
Molineaux, Susan M.
Weidner, Jeffrey R.
Aunins, John
(B) TITLE: A novel heterodimeric cysteine protease is required for interleukin-1beta processing in monocytes
(C) JOURNAL: Nature
(D) VOLUME: 356
(F) PAGES: 768-774
(G) DATE: 30-APR-1992
(K) RELEVANT RESIDUES IN SEQ ID NO: 3: FROM 1 TO 20

(xi) SEQUENCE DESCRIPTION: SEQ ID NO: 3:

ACATGACTAC AGAGCTGGAG 20

(2) INFORMATION FOR SEQ ID NO: 4:

(i) SEQUENCE CHARACTERISTICS:

(A) LENGTH: 20
(B) TYPE: nucleic acid
(C) STRANDEDNESS: single
(D) TOPOLOGY: linear (ii) MOLECULE TYPE: DNA (x) PUBLICATION INFORMATION:
(A) AUTHORS: Thornberry, Nancy A.
Bull, Herbert G.
Calaycay, Jimmy R.
Chapman, Kevin T.
Howard, Andrew D.
Kostura, Matthew J.
Miller, Douglas K.
Molineaux, Susan M.
Weidner, Jeffrey R.
Aunins, John
(B) TITLE: A novel heterodimeric cysteine protease is required for interleukin-1beta processing in monocytes
(C) JOURNAL: Nature
(D) VOLUME: 356
(F) PAGES: 768-774
(G) DATE: 30-APR-1992

(xi) SEQUENCE DESCRIPTION: SEQ ID NO: 4:

```
CACCACGGCA GGCCTGGATG                                              20
```

(2) INFORMATION FOR SEQ ID NO: 5:

(i) SEQUENCE CHARACTERISTICS:
(A) LENGTH: 235
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Homo sapiens (xi) SEQUENCE DESCRIPTION: SEQ ID NO: 5:

```
GAAATGACTA CAGAGCTGGA GGCATTTGCT CACCGCCCAG AGCACAAGAC CTCTGACAGC    60

ACCTTCCCGG TGTTCTTGTC TCATGGTGTT CGGGAAGGCA TTTGTGGGAA GAAATACTCT   120

GAACAAGTCC CTGATATATT ACAATTCAAT GAAATATTTA AAATGTTGAA TAGCAAGAAC   180

TGCCCAAGTT TGAAGGACAA ACCCAAGGTG ATCATCTTCG AGGCCTGCTG TGGTG        235
```

(2) INFORMATION FOR SEQ ID NO: 6:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 5 from 8 to 30

(xi) SEQUENCE DESCRIPTION: SEQ ID NO: 6:

```
CTACAGAGCT GGAGGCATTT GCT                                           23
```

(2) INFORMATION FOR SEQ ID NO: 7:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: DNA (x) PUBLICATION INFORMATION:
(A) AUTHORS: Thornberry, Nancy A.
Bull, Herbert G.
Calaycay, Jimmy R.
Chapman, Kevin T.
Howard, Andrew D.
Kostura, Matthew J.
Miller, Douglas K.
Molineaux, Susan M.
Weidner, Jeffrey R.
Aunins, John
(B) TITLE: A novel heterodimeric cysteine protease is required for interleukin-1beta processing in monocytes
(C) JOURNAL: Nature
(D) VOLUME: 356
(F) PAGES: 768-774
(G) DATE: 30-APR-1992

(xi) SEQUENCE DESCRIPTION: SEQ ID NO: 7:

TTAATGTCCT GGGAAGAGGT AGAA 24

(2) INFORMATION FOR SEQ ID NO: 8:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 753 to 773

(xi) SEQUENCE DESCRIPTION: SEQ ID NO: 8:

GAGGCAGTTG CGGTTGTTGA A 21

(2) INFORMATION FOR SEQ ID NO: 9:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 829 to 849

(xi) SEQUENCE DESCRIPTION: SEQ ID NO: 9:

CTCTGACCCA CAGTTCCCCA C 21

(2) INFORMATION FOR SEQ ID NO: 10:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 from 695 to 711

(xi) SEQUENCE DESCRIPTION: SEQ ID NO: 10:

AACTGTGCAT GATGAGA 17

(2) INFORMATION FOR SEQ ID NO: 11:

(i) SEQUENCE CHARACTERISTICS:
(A) LENGTH: 19
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 11:

AGATGCTGTG TACAAGACC 19

(2) INFORMATION FOR SEQ ID NO: 12:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 795 to 811

(xi) SEQUENCE DESCRIPTION: SEQ ID NO: 12:

GCCTGGACAA TGATGAC 17

(2) INFORMATION FOR SEQ ID NO: 13:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 995 to 1011

(xi) SEQUENCE DESCRIPTION: SEQ ID NO: 13:

TGATGAAGAT AGAGCCC 17

(2) INFORMATION FOR SEQ ID NO: 14:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 from 204 to 220

(xi) SEQUENCE DESCRIPTION: SEQ ID NO: 14:

CGGGTCATGG CAGACTC 17

(2) INFORMATION FOR SEQ ID NO: 15:

(i) SEQUENCE CHARACTERISTICS:
(A) LENGTH: 17
(B) TYPE: nucleic acid
(C) STRANDEDNESS: single (D) TOPOLOGY: linear (ii) MOLECULE TYPE: DNA (ix) FEATURE:
(D) OTHER INFORMATION: SEQ ID NO: 1 complementary from 249 to 265

(xi) SEQUENCE DESCRIPTION: SEQ ID NO: 15:

GTTTGAAGAA GCATTTG 17

(2) INFORMATION FOR SEQ ID NO: 16:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 from 330 to 346

(xi) SEQUENCE DESCRIPTION: SEQ ID NO: 16:

CCTGAGTCAG GAGAATC 17

(2) INFORMATION FOR SEQ ID NO: 17:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 375 to 391

(xi) SEQUENCE DESCRIPTION: SEQ ID NO: 17:

AGTCTCAGGA ATTCTTC 17

(2) INFORMATION FOR SEQ ID NO: 18:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 from 503 to 519

(xi) SEQUENCE DESCRIPTION: SEQ ID NO: 18:

AGCTGACTTT GACATCA 17

(2) INFORMATION FOR SEQ ID NO: 19:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 1 complementary from 587 to 603

(xi) SEQUENCE DESCRIPTION: SEQ ID NO: 19:

```
GCGCTGACTC CATATCC                                              17
```

(2) INFORMATION FOR SEQ ID NO: 20:

(i) SEQUENCE CHARACTERISTICS:
(A) LENGTH: 33
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 20:

```
CGCGGATCCA CCATGGCAGA AGGCAACCAC AGA                            33
```

(2) INFORMATION FOR SEQ ID NO: 21:

(i) SEQUENCE CHARACTERISTICS:
(A) LENGTH: 39
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 21:

```
GGCTCTAGAC TCGAGTTATC AATTGCCAGG AAAGAGGTA                      39
```

(2) INFORMATION FOR SEQ ID NO: 22:

(i) SEQUENCE CHARACTERISTICS:
(A) LENGTH: 1310
(B) TYPE: nucleic acid
(C) STRANDEDNESS: single
(D) TOPOLOGY: linear (ii) MOLECULE TYPE: cDNA (ix) FEATURE:
(A) NAME/KEY: CDS (xi) SEQUENCE DESCRIPTION: SEQ ID NO: 22:

```
GAACAACGTG GCTGGACAAA CATCTATCCA GACCCTAGTA CCTAATACGG ATCAAAAGTC     60

GACCAGTGTA AAAAAAGACA ACCACAAAAA AAAAACAGTT AAG ATG TTG GAA TAC      115
                                                Met Leu Glu Tyr
                                                  1

CTG GGC AAA GAT GTT CTT CAT GGT GTT TTT AAT TAT TTG GCA AAA CAC      163
Leu Gly Lys Asp Val Leu His Gly Val Phe Asn Tyr Leu Ala Lys His
  5                  10                  15                  20

GAT GTT CTG ACA TTG AAG GAA GAG GAA AAG AAA AAA TAT TAT GAT GCC      211
Asp Val Leu Thr Leu Lys Glu Glu Glu Lys Lys Lys Tyr Tyr Asp Ala
                 25                  30                  35

AAA ATT GAA GAC AAG GCC CTG ATC TTG GTA GAC TCT TTG CGA AAG AAT      259
Lys Ile Glu Asp Lys Ala Leu Ile Leu Val Asp Ser Leu Arg Lys Asn
             40                  45                  50

CGC GTG GCT CAT CAA ATG TTT ACC CAA ACA CTT CTC AAT ATG GAC CAA      307
Arg Val Ala His Gln Met Phe Thr Gln Thr Leu Leu Asn Met Asp Gln
         55                  60                  65

AAG ATC ACC AGT GTA AAA CCT CTT CTG CAA ATC GAG GCT GGA CCA CCT      355
Lys Ile Thr Ser Val Lys Pro Leu Leu Gln Ile Glu Ala Gly Pro Pro
     70                  75                  80

GAG TCA GCA GAA TCT ACA AAT ATA CTC AAA CTT TGT CCT CGT GAA GAA      403
Glu Ser Ala Glu Ser Thr Asn Ile Leu Lys Leu Cys Pro Arg Glu Glu
```

```
 85                  90                  95                 100

TTC CTG AGA CTG TGT AAA AAA AAT CAT GAT GAG ATC TAT CCA ATA AAA       451
Phe Leu Arg Leu Cys Lys Lys Asn His Asp Glu Ile Tyr Pro Ile Lys
                105                 110                 115

AAG AGA GAG GAC CGC AGA CGC CTG GCT CTC ATC ATA TGC AAT ACA AAG       499
Lys Arg Glu Asp Arg Arg Arg Leu Ala Leu Ile Ile Cys Asn Thr Lys
            120                 125                 130

TTT GAT CAC CTG CCT GCA AGG AAT GGG GCT CAC TAT GAC ATC GTG GGG       547
Phe Asp His Leu Pro Ala Arg Asn Gly Ala His Tyr Asp Ile Val Gly
        135                 140                 145

ATG AAA AGG CTG CTT CAA GGC CTG GGC TAC ACT GTG GTT GAC GAA AAG       595
Met Lys Arg Leu Leu Gln Gly Leu Gly Tyr Thr Val Val Asp Glu Lys
    150                 155                 160

AAT CTC ACA GCC AGG GAT ATG GAG TCA GTG CTG AGG GCA TTT GCT GCC       643
Asn Leu Thr Ala Arg Asp Met Glu Ser Val Leu Arg Ala Phe Ala Ala
165                 170                 175                 180

AGA CCA GAG CAC AAG TCC TCT GAC AGC ACG TTC TTG GTA CTC ATG TCT       691
Arg Pro Glu His Lys Ser Ser Asp Ser Thr Phe Leu Val Leu Met Ser
                185                 190                 195

CAT GGC ATC CTA GAG GGA ATC TGC GGA ACT GCG CAT AAA AAG AAA AAA       739
His Gly Ile Leu Glu Gly Ile Cys Gly Thr Ala His Lys Lys Lys Lys
            200                 205                 210

CCG GAT GTG CTG CTT TAT GAC ACC ATC TTC CAG ATA TTC AAC AAC CGC       787
Pro Asp Val Leu Leu Tyr Asp Thr Ile Phe Gln Ile Phe Asn Asn Arg
        215                 220                 225

AAC TGC CTC AGT CTA AAG GAC AAA CCC AAG GTC ATC ATT GTC CAG GCC       835
Asn Cys Leu Ser Leu Lys Asp Lys Pro Lys Val Ile Ile Val Gln Ala
    230                 235                 240

TGC AGA GGT GAA AAA CAT GGG GAA CTC TGG GTC AGA GAC TCT CCA GCA       883
Cys Arg Gly Glu Lys His Gly Glu Leu Trp Val Arg Asp Ser Pro Ala
245                 250                 255                 260

TCC TTG GCA CTC ATC TCT TCA CAG TCA TCT GAG AAC CTG GAG GCA GAT       931
Ser Leu Ala Leu Ile Ser Ser Gln Ser Ser Glu Asn Leu Glu Ala Asp
                265                 270                 275

TCT GTT TGC AAG ATC CAC GAG GAG AAG GAC TTC ATT GCT TTC TGT TCT       979
Ser Val Cys Lys Ile His Glu Glu Lys Asp Phe Ile Ala Phe Cys Ser
            280                 285                 290

TCA ACA CCA CAT AAC GTG TCC TGG AGA GAC CGC ACA AGG GGC TCC ATC      1027
Ser Thr Pro His Asn Val Ser Trp Arg Asp Arg Thr Arg Gly Ser Ile
        295                 300                 305

TTC ATT ACG GAA CTC ATC ACA TGC TTC CAG AAA TAT TCT TGC TGC TGC      1075
Phe Ile Thr Glu Leu Ile Thr Cys Phe Gln Lys Tyr Ser Cys Cys Cys
    310                 315                 320

CAC CTA ATG GAA ATA TTT CGG AAG GTA CAG AAA TCA TTT GAA GTT CCA      1123
His Leu Met Glu Ile Phe Arg Lys Val Gln Lys Ser Phe Glu Val Pro
325                 330                 335                 340

CAG GCT AAA GCC CAG ATG CCC ACC ATA GAA CGA GCA ACC TTG ACA AGA      1171
Gln Ala Lys Ala Gln Met Pro Thr Ile Glu Arg Ala Thr Leu Thr Arg
                345                 350                 355

GAT TTC TAC CTC TTT CCT GGC AAT TGAAAATGAA ACCACAGGCA GCCCAGCCCT     1225
Asp Phe Tyr Leu Phe Pro Gly Asn
            360

CCTCTGTCAA CATCAAAGAG CACATTTACC AGTATAGCTT GCATAGTCAA TATTTGGTAT   1285

TTCAATAAAA GTAAAGACTG TATCT                                         1310
```

(2) INFORMATION FOR SEQ ID NO: 23:

(i) SEQUENCE CHARACTERISTICS:

(A) LENGTH: 364

(B) TYPE: amino acid

```
        (D) TOPOLOGY: linear

   (ii) MOLECULE TYPE: protein

   (xi) SEQUENCE DESCRIPTION: SEQ ID NO: 23:

Met Leu Glu Tyr Leu Gly Lys Asp Val Leu His Gly Val Phe Asn Tyr
  1               5                  10                  15

Leu Ala Lys His Asp Val Leu Thr Leu Lys Glu Glu Glu Lys Lys Lys
             20                  25                  30

Tyr Tyr Asp Ala Lys Ile Glu Asp Lys Ala Leu Ile Leu Val Asp Ser
         35                  40                  45

Leu Arg Lys Asn Arg Val Ala His Gln Met Phe Thr Gln Thr Leu Leu
     50                  55                  60

Asn Met Asp Gln Lys Ile Thr Ser Val Lys Pro Leu Leu Gln Ile Glu
 65                  70                  75                  80

Ala Gly Pro Pro Glu Ser Ala Glu Ser Thr Asn Ile Leu Lys Leu Cys
                 85                  90                  95

Pro Arg Glu Glu Phe Leu Arg Leu Cys Lys Lys Asn His Asp Glu Ile
            100                 105                 110

Tyr Pro Ile Lys Lys Arg Glu Asp Arg Arg Arg Leu Ala Leu Ile Ile
        115                 120                 125

Cys Asn Thr Lys Phe Asp His Leu Pro Ala Arg Asn Gly Ala His Tyr
    130                 135                 140

Asp Ile Val Gly Met Lys Arg Leu Leu Gln Gly Leu Gly Tyr Thr Val
145                 150                 155                 160

Val Asp Glu Lys Asn Leu Thr Ala Arg Asp Met Glu Ser Val Leu Arg
                165                 170                 175

Ala Phe Ala Ala Arg Pro Glu His Lys Ser Ser Asp Ser Thr Phe Leu
            180                 185                 190

Val Leu Met Ser His Gly Ile Leu Glu Gly Ile Cys Gly Thr Ala His
        195                 200                 205

Lys Lys Lys Lys Pro Asp Val Leu Leu Tyr Asp Thr Ile Phe Gln Ile
    210                 215                 220

Phe Asn Asn Arg Asn Cys Leu Ser Leu Lys Asp Lys Pro Lys Val Ile
225                 230                 235                 240

Ile Val Gln Ala Cys Arg Gly Glu Lys His Gly Glu Leu Trp Val Arg
                245                 250                 255

Asp Ser Pro Ala Ser Leu Ala Leu Ile Ser Ser Gln Ser Ser Glu Asn
            260                 265                 270

Leu Glu Ala Asp Ser Val Cys Lys Ile His Glu Glu Lys Asp Phe Ile
        275                 280                 285

Ala Phe Cys Ser Ser Thr Pro His Asn Val Ser Trp Arg Asp Arg Thr
    290                 295                 300

Arg Gly Ser Ile Phe Ile Thr Glu Leu Ile Thr Cys Phe Gln Lys Tyr
305                 310                 315                 320

Ser Cys Cys Cys His Leu Met Glu Ile Phe Arg Lys Val Gln Lys Ser
                325                 330                 335

Phe Glu Val Pro Gln Ala Lys Ala Gln Met Pro Thr Ile Glu Arg Ala
            340                 345                 350

Thr Leu Thr Arg Asp Phe Tyr Leu Phe Pro Gly Asn
        355                 360


(2) INFORMATION FOR SEQ ID NO: 24:

     (i) SEQUENCE CHARACTERISTICS:
          (A) LENGTH: 19
```

(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 685 to 703

(xi) SEQUENCE DESCRIPTION: SEQ ID NO: 24:

CATGTCTCAT GGCATCCTA 19

(2) INFORMATION FOR SEQ ID NO: 25:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 712 to 731

(xi) SEQUENCE DESCRIPTION: SEQ ID NO: 25:

CTGCGGAACT GCGCATAAAA 20

(2) INFORMATION FOR SEQ ID NO: 26:

(i) SEQUENCE CHARACTERISTICS:
(A) LENGTH: 35
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 26:

GGCTCTAGAC TCGAGGTGCT CTTTGATGTT GACAG 35

(2) INFORMATION FOR SEQ ID NO: 27:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 939 to 958

(xi) SEQUENCE DESCRIPTION: SEQ ID NO: 27:

CTTCTCCTCG TGGATCTTGC 20

(2) INFORMATION FOR SEQ ID NO: 28:

(i) SEQUENCE CHARACTERISTICS:
(A) LENGTH: 16
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 124 to 139

(xi) SEQUENCE DESCRIPTION: SEQ ID NO: 28:

AGATGTTCTT CATGGT 16

(2) INFORMATION FOR SEQ ID NO: 29:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 290 to 306

(xi) SEQUENCE DESCRIPTION: SEQ ID NO: 29:

CTTCTCAATA TGGACCA 17

(2) INFORMATION FOR SEQ ID NO: 30:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 472 to 488

(xi) SEQUENCE DESCRIPTION: SEQ ID NO: 30:

CCTGGCTCTC ATCATAT 17

(2) INFORMATION FOR SEQ ID NO: 31:

(i) SEQUENCE CHARACTERISTICS:
(A) LENGTH: 18
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 634 to 651

(xi) SEQUENCE DESCRIPTION: SEQ ID NO: 31:

ATTTGCTGCC AGACCAGA 18

(2) INFORMATION FOR SEQ ID NO: 32:

(i) SEQUENCE CHARACTERISTICS:
(A) LENGTH: 19
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 833 to 851

(xi) SEQUENCE DESCRIPTION: SEQ ID NO: 32:

GCCTGCAGAG GTGAAAAAC 19

(2) INFORMATION FOR SEQ ID NO: 33:

(i) SEQUENCE CHARACTERISTICS:
(A) LENGTH: 19

(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 from 1020 to 1038

(xi) SEQUENCE DESCRIPTION: SEQ ID NO: 33:

GCTCCATCTT CATTACGGA 19

(2) INFORMATION FOR SEQ ID NO: 34:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 1094 to 1110

(xi) SEQUENCE DESCRIPTION: SEQ ID NO: 34:

GATTTCTGTA CCTTCCG 17

(2) INFORMATION FOR SEQ ID NO: 35:

(i) SEQUENCE CHARACTERISTICS:
(A) LENGTH: 16
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 715 to 730

(xi) SEQUENCE DESCRIPTION: SEQ ID NO: 35:

TTTATGCGCA GTTCCG 16

(2) INFORMATION FOR SEQ ID NO: 36:

(i) SEQUENCE CHARACTERISTICS:
(A) LENGTH: 18
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 521 to 538

(xi) SEQUENCE DESCRIPTION: SEQ ID NO: 36:

GTCATAGTGA GCCCCATT 18

(2) INFORMATION FOR SEQ ID NO: 37:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 385 to 401

(xi) SEQUENCE DESCRIPTION: SEQ ID NO: 37:

CTTCACGAGG ACAAAGT 17

(2) INFORMATION FOR SEQ ID NO: 38:

(i) SEQUENCE CHARACTERISTICS:
(A) LENGTH: 17
(B) TYPE: nucleic acid
(C) STRANDEDNESS: single
(D) TOPOLOGY: linear (ii) MOLECULE TYPE: DNA (ix) FEATURE:
(D) OTHER INFORMATION: SEQ ID NO: 22 complementary from 237 to 253

(xi) SEQUENCE DESCRIPTION: SEQ ID NO: 38:

TCGCAAAGAG TCTACCA 17

(2) INFORMATION FOR SEQ ID NO: 39:

(i) SEQUENCE CHARACTERISTICS:
(A) LENGTH: 33
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 39:

CGCGGATCCA AGATGTTGGA ATACCTGGGC AAA 33

(2) INFORMATION FOR SEQ ID NO: 40:

(i) SEQUENCE CHARACTERISTICS:
(A) LENGTH: 68
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 40:

CGCGGATCCA CCATGGCTTC TATGACAGGA GGTCAACAAA TGGGACAAAA GATCACCAGT 60

GTAAAACC 68

(2) INFORMATION FOR SEQ ID NO: 41:

(i) SEQUENCE CHARACTERISTICS:
(A) LENGTH: 36
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 41:

ATGTTTTTCA CCTCTGGAGG CCTGGACAAT GATGAC 36

(2) INFORMATION FOR SEQ ID NO: 42:

(i) SEQUENCE CHARACTERISTICS:

-continued

```
        (A) LENGTH: 36
        (B) TYPE: nucleic acid
        (C) STRANDEDNESS: single
        (D) TOPOLOGY: linear

   (ii) MOLECULE TYPE: DNA

   (xi) SEQUENCE DESCRIPTION: SEQ ID NO: 42:

GTCATCATTG TCCAGGCCTC CAGAGGTGAA AAACAT                        36
```

DNA SEQUENCES CODING FOR THE HUMAN PROTEINS TX AND TY RELATED TO THE INTERLEUKIN-1β CONVERTING ENZYME

PRIOR APPLICATION

This application is the national phase of PCT application No. FR95/01035 filed Aug. 1, 1995.

The present invention relates to a DNA sequence coding for a new human protein Tx related to the interleukin-1beta converting enzyme, the protein Tx, their production process, the pharmaceutical compositions containing it and their uses as medicaments.

Interleukin-1beta (IL-1β) is a pro-inflammatory cytokine involved in the pathogenesis of multiple acute or chronic inflammatory illnesses such as rheumatoid arthritis, inflammatory illnesses of the intestines or the septic shock (Dinarello et al., 1992, Immunological Reviews, 127, 119–146).

The human monocytes and macrophages synthesize IL-1β in the form of an inactive precursor of 31 kDa (pIL-1β). The pIL-1β does not have the conventional signal sequence and can only be secreted efficiently by the cell after cleavage between the aspartic acid 116 and the alanine 117. This cleavage, which generates the active IL-1β form of 17 kDa, is carried out by a specific enzyme called interleukin-1beta converting enzyme (ICE) (Thornberry et al., 1992, Nature, 356, 768–774; Cerretti et al., 1992, Science, 256, 97–100). This enzyme has been characterized and cloned in man and in mice (Nett et al., 1992, Journal of Immunology, 149, 3254–3259; Molineaux et al., 1993, Proc. Natl. Acad. Sci. USA, 90, 1809–1813). It is a unique cysteine protease which has no homology with other known thiol-proteases. It also possesses a particular specificity for certain Asp-X peptide bonds of pIL-1β.

The ICE enzyme is composed of two sub-units of 20 kDa (p20) and 10 kDa (p10) whose combination is necessary for enzymatic activity. These sub-units originate from the proteolytic cleavage of a pro-enzyme form of 45 kDa (p45). The ICE enzyme itself is capable of cleaving its precursor p45 or the p30 form of 30 kDa, which does not have the 119 amino acids of the N-terminal part of the pro-enzyme, in the p20 plus the p10 active form. The complete sequence of p45 has been characterized by its cDNA as well as the amino acid sequence (Thornberry et al. already quoted). The characterization of the gene of human ICE has been described (Cerretti et al., 1994, Genomics, 20, 468–473).

Recent work has revealed a possible role of ICE in the regulation of programmed cellular death or apoptosis (Yuan et al., 1993, Cell, 75, 641–652). In fact, ICE has a 28% homology with Ced-3, a protein of *C. elegans* involved in apoptosis and the superexpression of murine ICE in rat fibroblasts which triggers apoptosis (Miura et al., 1993, Cell, 75, 653–660). Moreover, the expression of the protein crmA, an inhibiting viral serpine of ICE, in ganglioneurons of transfected chickens protects these cells from death by apoptosis induced by the suppression of growth factor (nerve growth factor) (Gagliardini et al., 1994, Science, 263, 826–828). These observations suggest that ICE or homologues of this protein could be involved in the regulation of programmed cellular death observed in particular in degenerative neuronal illnesses such as Alzheimer's disease or Parkinson's disease as well as in cerebral ischemia (Barinaga, M, Science, 259, 762, 1993).

The revelation of new proteins related to ICE playing a role either in the maturation of IL-1β or in apoptosis may contribute to the development of new therapeutic or diagnostic agents in situations in which IL-1β or apoptosis are involved.

The present invention relates to a new human protein Tx which has an approximately 52% homology with the human precursor p45 of ICE and which does not allow the maturation of the precursor of IL-1β into active cytokine. The protein Tx has two unexpected functions: on the one hand, it is a protease and it is in particular capable of cleaving the precursor p30 of ICE into sub-units p10 and p20 and on the other hand, it is capable of inducing apoptosis in cells, for example in transfected Cos cells.

These biological properties allow the use of the protein Tx to be anticipated in the treatment of pathological situations which respond to IL-1β or in which apoptosis occurs.

The present invention also relates to a new human protein Ty which has a homology of greater than 70% with the protein Tx. The protein Ty is capable of inducing apoptosis in cells, for example, in transfected Cos cells. The protein Ty is a protease which is capable of self-cleaving in an intermolecular manner.

Therefore a subject of the present invention is a DNA sequence containing a DNA sequence coding for a human polypeptide having a protease activity and having the nucleotide sequence of the sequence SEQ ID NO: 1:

```
GCTCTTTCCA ACGCTGTAAA AAAGGACAGA GGCTGTTCCC T ATG GCA GAA GGC         53
                                              Met Ala Glu Gly
                                                1

AAC CAC AGA AAA AAG CCA CTT AAG GTG TTG GAA TCC CTG GGC AAA GAT       101
Asn His Arg Lys Lys Pro Leu Lys Val Leu Glu Ser Leu Gly Lys Asp
  5                  10                  15                  20

TTC CTC ACT GGT GTT TTG GAT AAC TTG GTG GAA CAA AAT GTA CTG AAC       149
Phe Leu Thr Gly Val Leu Asp Asn Leu Val Glu GLn Asn Val Leu Asn
                 25                  30                  35

TGG AAG GAA GAG GAA AAA AAG AAA TAT TAC GAT GCT AAA ACT GAA GAC       197
Trp Lys Glu Glu Glu Lys Lys Lys Tyr Tyr Asp Ala Lys Thr Glu Asp
             40                  45                  50

AAA GTT CGG GTC ATG GCA GAC TCT ATG CAA GAG AAG CAA CGT ATG GCA       245
Lys Val Arg Val Met Ala Asp Ser Met Gln Glu Lys Gln Arg Met Ala
         55                  60                  65

GGA CAA ATG CTT CTT CAA ACC TTT TTT AAC ATA GAC CAA ATA TCC CCC       293
```

-continued

Gly Gln Met Leu Leu Gln Thr Phe Phe Asn Ile Asp Gln Ile Ser Pro
70 75 80

AAT AAA AAA GCT CAT CCG AAT ATG GAG GCT GGA CCA CCT GAG TCA GGA 341
Asn Lys Lys Ala His Pro Asn Met Glu Ala Gly Pro Pro Glu Ser Gly
85 90 95 100

GAA TCT ACA GAT GCC CTC AAG CTT TGT CCT CAT GAA GAA TTC CTG AGA 389
Glu Ser Thr Asp Ala Leu Lys Leu Cys Pro His Glu Glu Phe Leu Arg
105 110 115

CTA TGT AAA GAA AGA GCT GAA GAG ATC TAT CCA ATA AAG GAG AGA AAC 437
Leu Cys Lys Glu Arg Ala Glu Glu Ile Tyr Pro Ile Lys Glu Arg Asn
120 125 130

AAC CGC ACA CGC CTG GCT CTC ATC ATA TGC AAT ACA GAG TTT GAC CAT 485
Asn Arg Thr Arg Leu Ala Leu Ile Ile Cys Asn Thr Glu Phe Asp His
135 140 145

CTG CCT CCG AGG AAT GGA GCT GAC TTT GAC ATC ACA GGG ATG AAG GAG 533
Leu Pro Pro Arg Asn Gly Ala Asp Phe Asp Ile Thr Glu Met Lys Glu
150 155 160

CTA CTT GAG GGT CTG GAC TAT AGT GTA GAT GTA GAA GAG AAT CTG ACA 581
Leu Leu Glu Gly Leu Asp Tyr Ser Val Asp Val Glu Glu Asn Leu Thr
165 170 175 180

GCC AGG GAT ATG GAG TCA GCG CTG AGG GCA TTT GCT ACC AGA CAA GAG 629
Ala Arg Asp Met Glu Ser Ala Leu Arg Ala Phe Ala Thr Arg Pro Glu
185 190 195

CAC AAG TCC TCT GAC AGC ACA TTC TTG GTA CTC ATG TCT CAT GGC ATC 677
His Lys Ser Ser Asp Ser Thr Phe Leu Val Leu Met Ser His Gly Ile
200 205 210

CTG GAG GGA ATC TGC GGA ACT GTG CAT GAT GAG AAA AAA CCA GAT GTG 725
Leu Glu Gly Ile Cys Gly Thr Val His Asp Glu Lys Lys Pro Asp Val
215 220 225

CTG CTT TAT GAC ACC ATC TTC CAG ATA TTC AAC AAC CGC AAC TCG CTC 773
Leu Leu Tyr Asp Thr Ile Phe Gln Ile Phe Asn Asn Arg Asn Cys Leu
230 235 240

AGT CTG AAG GAC AAA CCC AAG GTC ATC ATT GTC CAG GCC TGC AGA GGT 821
Ser Leu Lys Asp Lys Pro Lys Val Ile Ile Val Gln Ala Cys Arg Gly
245 250 255 260

GCA AAC CGT GGG GAA CTG TGG GTC AGA GAC TCT CCA GCA TCC TTG GAA 869
Ala Asn Arg Gly Glu Leu Trp Val Arg Asp Ser Pro Ala Ser Leu Glu
265 270 275

GTG GCC TCT TCA CAG TCA TCT GAG AAC CTG GAG GAA GAT GCT GTT TAC 917
Val Ala Ser Ser Gln Ser Ser Glu Asn Leu Glu Glu Asp Ala Val Tyr
280 285 290

AAG ACC CAC GTG GAG AAG GAC TTC ATT GCT TTC TGC TCT TCA ACG CCA 965
Lys Thr His Val Glu Lys Asp Phe Ile Ala Phe Cys Ser Ser Thr Pro
295 300 305

CAC AAC GTG TCC TGG AGA GAC AGC ACA ATG GGC TCT ATC TTC ATC ACA 1013
His Asn Val Ser Trp Arg Asp Ser Thr Met Gly Ser Ile Phe Ile Thr
310 315 320

CAA CTC ATC ACA TGC TTC CAG AAA TAT TCT TGG TGC TGC CAC CTA GAG 1061
Glu Leu Ile Thr Cys Phe Gln Lys Tyr Ser Trp Cys Cys His Leu Glu
325 330 335 340

GAA GTA TTT CGG AAG GTA CAG CAA TCA TTT GAA ACT CCA AGG GCC AAA 1109
Glu Val Phe Arg Lys Val Gln Gln Ser Phe Glu Thr Pro Arg Ala Lys
345 350 355

GCT CAA ATG CCC ACC ATA GAA CGA CTG TCC ATG ACA AGA TAT TTC TAC 1557
Ala Gln Met Pro Thr Ile Glu Arg Leu Ser Met Thr Arg Tyr Phe Tyr
360 365 370

-continued

```
CTC TTT CCT GGC AAT TGAAAATGGA AGCCACAAGC AGCCCAGCCC TCCTTAATCA   1212
Leu Phe Pro Gly Asn
        375

ACTTCAAGGA GCACCTTCAT TAGTACAGCT TGCATATTTA ACATTTTGTA TTTCAATAAA 1272

AGTGAAGACA AAAAAAAAA                                              1291
```

as well as a DNA sequence containing a DNA sequence coding for a human polypeptide having the capacity to induce apoptosis and having the nucleotide sequence of the sequence SEQ ID NO: 1 above.

A particular subject of the invention is a DNA sequence coding for a human polypeptide having a protease activity and capable of inducing apoptosis and having the nucleotide sequence of the sequence SEQ ID NO: 1 above.

The above DNA sequence which codes for a protein having 377 amino acids is a cDNA sequence which can be obtained by amplification using PCR, starting from the RNA of monocytes activated by LPS or of human polynuclear cells or placenta, thanks to the oligonucleotide derivatives of the sequence of ICE and the sequence of homologous genes identified previously, according to the operating conditions a precise description of which is given further on.

The revelation of protease activity as well as that of the capacity to induce apoptosis are illustrated further on in the experimental part.

A more particular subject of the invention is a DNA sequence coding for a human polypeptide having a protease activity and capable of inducing apoptosis having the sequence which begins at nucleotide 42 and ends at nucleotide 1172 of the sequence SEQ ID NO: 1 as well as DNA sequences which hybridize with it and having the same function.

Within sequences which hybridize, DNA sequences are included which hybridize under high stringency conditions and which code for a polypeptide having the same activity. The stringency conditions include for example a hybridization at 65° C., for 18 hours in a 5×SSPE; 10×Denhardt; 100 μg/ml DNAss; 1% SDS solution followed by 3 washings for 5 minutes with 2×SSC; 0.05% SDS, then 3 washings for 15 minutes at 65° C. in 1×SSC; 0.1% SDS, according to Maniatis et al., Molecular cloning, Cold Spring Harbor Laboratory Press, 1989.

A quite particular subject of the invention is the DNA sequence having the sequence beginning at nucleotide 42 and ending at nucleotide 1172 of the sequence SEQ ID NO: 1.

Knowledge of the sequence SEQ ID NO: 1 allows the present invention to be reproduced for example by known methods of chemical synthesis or by screening of a gene library or a cDNA library using synthetic oligonucleotide probes by known hybridization techniques.

The invention also relates to a human polypeptide having a protease activity and capable of inducing apoptosis and having the amino acid sequence of the sequence SEQ ID NO: 2:

```
Met Ala Glu Gly Asn His Arg Lys Lys Pro Leu Lys Val Leu Glu Ser
 1               5                  10                  15

Leu Gly Lys Asp Phe Leu Thr Gly Val Leu Asp Asn Leu Val Glu Gln
            20                  25                  30

Asn Val Leu Asn Trp Lys Glu Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
 65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
```

-continued

```
        195                 200                 205

Ser His Gly Ile Leu Glu Gly Ile Cys Gly Thr Val His Asp Glu Lys
    210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375
```

as well as the alleles and analogues of this sequence.

Within alleles and analogues, sequences are included which are modified by the substitution, deletion or addition of one or more amino acids in sofar as these products retain the same function.

A special subject of the invention is the polypeptide having the amino acid sequence of the sequence SEQ ID NO: 2 and designated protein Tx.

One of the aspects of the invention also relates to a polypeptide according to the invention as obtained by the expression in a host cell of a DNA coding for the amino acid sequence of the sequence SEQ ID NO: 2.

When the polypeptide according to the invention is obtained by expression in a host cell, it is carried out according to known methods of genetic engineering and cell culture.

The expression can be carried out in a prokaryotic cell, for example *E. coli* or in a eukaryotic cell, for example a Cos cell containing the DNA sequence coding for the polypeptide of the invention preceded by a suitable promoter sequence.

The invention relates in particular to a polypeptide according to the invention as obtained by the expression in a eukaryotic host cell.

Quite particularly the invention relates to a polypeptide according to the invention the protease activity of which corresponds to the capacity for maturation of the conversion enzyme of IL-1beta. An example of determination of this particular protease activity is described further on.

A subject of the invention is also an expression vector containing a DNA sequence coding for a human polypeptide having a protease activity and capable of inducing apoptosis as well as a host cell transformed by an above vector.

Expression vectors are known vectors which allow the expression of the protein under the control of a suitable promoter. For prokaryotic cells, the promoter can be for example the lac promoter, the trp promoter, the tac promoter, the $\beta$-lactamase promoter or the PL promoter. For yeast cells, the promoter can be for example the PGK promoter or the AD promoter. For mammalian cells, the promoter can be for example the SV40 promoter or promoters of the adenovirus. Baculovirus-type vectors can also be used for expression in insect cells.

The host cells are for example prokaryotic cells or eukaryotic cells. The prokaryotic cells are for example *E. coli,* Bacillus or Streptomyces. The eukaryotic host cells include yeasts as well as cells of higher organisms, for example mammalian cells or insect cells. The mammalian cells are for example fibroblasts such as hamster CHO or BHK cells and monkey Cos cells. The insect cells are for example SF9 cells.

The invention relates to a process which includes the expression of the protein Tx in a host cell transformed by a DNA coding for the amino acid sequence of the sequence SEQ ID NO: 2 and in particular a process in which the host cell is a eukaryotic cell.

A subject of the invention is also antibodies directed against the polypeptide according to the invention.

The polyclonal or monoclonal antibodies according to the invention can be prepared according to known methods and can be used for example for the assay of the protein Tx, for example in an ELISA test, and as diagnosis agents.

The new protein Tx according to the invention has remarkable biological properties, in particular a protease activity, notably the capacity to mature the conversion enzyme of IL-1beta as well as the capacity to induce apoptosis, as shown by the results given further on.

These biological properties render the protein Tx according to the invention of use for example in the treatment of auto-immune diseases, in the healing of wounds or in the reduction of the side-effects of irradiation treatments in which IL-1$\beta$ is involved or for example in the area of cancers and infection in which apoptosis is involved.

Therefore a subject of the present invention is, as medicaments, the polypeptide according to the invention.

The invention extends to the pharmaceutical compositions containing as active ingredient a medicament defined above and particularly relates to pharmaceutical compositions for modulating the production of IL-1beta or for modulating apoptosis.

The active ingredient can be incorporated with the usual excipients for the preparation of the above pharmaceutical compositions. The compositions can be administered by parenteral, oral or local route.

The polypeptides according to the invention also allow new therapeutic agents to be envisaged constituted by inhibitors of these polypeptides and their use as a medicament, for example in the treatment of inflammation associated with auto-immune diseases, septic shock or neurodegenerative diseases.

A subject of the invention is also a DNA sequence hybridizing with the DNA sequence beginning at nucleotide 42 and ending at nucleotide 1172 of sequence SEQ ID NO: 1 and having the same function.

The hybridization is obtained for example in a buffer containing 5×SSC, 10×Denhardt, 100 microg/ml DNA of salmon sperm, 1% SDS, overnight at 65° C. Washings are then carried out for example in a buffer containing 1×SSC, 0.1% SDS, twice for 30 mn at 60° C.

The invention particularly relates to the DNA sequence coding for a polypeptide having a protease activity and capable of inducing apoptosis and having the nucleotide sequence of the sequence SEQ ID NO: 22 and more particularly the sequence beginning at nucleotide 104 and ending at nucleotide 1195 of the sequence SEQ ID NO: 22.

The DNA sequence SEQ ID NO: 22 above, which codes for a protein having 364 amino acids, is a cDNA sequence which can be obtained, for example, by amplification using PCR, from the cDNA of human spleen or placenta, thanks to the oligonucleotide derivatives of the Tx cDNA sequence (SEQ ID NO: 1). A detailed preparation example is given further on in the experimental part. The knowledge of the sequence SEQ ID NO: 22 allows the present invention to be reproduced for example by known methods of chemical synthesis or screening of gene libraries or cDNA libraries by oligonucleotide probes using hybridization techniques.

A subject of the invention is also a human polypeptide having a protease activity and capable of inducing apoptosis and having the amino acid sequence of the sequence SEQ ID NO: 23 and designated protein Ty.

One of the aspects of the invention also relates to a polypeptide according to the invention as obtained by the expression in a host cell of a DNA coding for the amino acid sequence of the sequence SEQ ID NO: 23.

The invention also includes the host cells, the expression vectors which allow the expression of the protein Ty to be obtained and examples of which have been indicated above for the expression of the protein Tx.

The invention also relates to a process which includes the expression of the protein Ty in a host cell transformed by a DNA coding for the amino acid sequence of the sequence SEQ ID NO: 23.

The invention also includes polyclonal antibodies or monoclonal antibodies directed against the protein Ty.

The invention also relates to the pharmaceutical compositions containing the protein Ty as a medicament.

BRIEF DESCRIPTION OF THE DRAWINGS

The attached figures illustrate certain aspects of the invention:

FIG. 2 represents the nucleotide sequence of exon 6 of the gene T2 (SEQ ID NO: 5).

FIG. 3 represents the nucleotide sequence of the Tx cDNA (SEQ ID NO: 1) and the corresponding amino acid sequence (SEQ ID NO: 2).

The following examples illustrate the invention without limiting it.

EXAMPLE 1

Identification of the Sequence Tx

A—Revelation of Genes Homologous to Human ICE

Genes homologous to ICE were identified by Southern Blot using a DNA probe corresponding to exon 6 of the ICE gene.

a) Preparation of the Exon 6 ICE Probe

The limits of the exon 6 of human ICE have been described as well as the complete intron/exon organization of the human ICE gene (Cerretti et al. already quoted). Exon 6 (235 bp) corresponds to nucleotides 635 to 868 of the cDNA sequence p45 of the described ICE (Thornberry et al. already quoted).

The exon 6 ICE probe was prepared by PCR amplification with the following oligonucleotides:

ICE 6.5: ACATGACTAC AGAGCTGGAG (SEQ ID NO: 3)

ICE 6.3: CACCACGGCA GGCCTGGATG (SEQ ID NO: 4)

which were chosen by using the published data (Thornberry et al. already quoted), synthesized and used to amplify by RT-PCR the RNA originating from human blood monocytes, extracted and purified using an RNA™ kit (Bioprobe), under the following amplification conditions: Enzyme Biotaq (BioProbe); 30 cycles (94° C., 1 mn; 60° C., 1 mn; 72° C., 1 mn); PCR apparatus: Perkin-Elmer (GeneAmp PCRsystem 9600).

The DNA exon 6 obtained was purified by centrifugation on a Spin X column (Costar) and labelled with $^{32}P$ using the random priming technique by means of the Oligolabelling kit (Pharmacia Biotech).

b) Hybridization to the Genomic DNA: Southern Blot

The radiolabelled exon 6 ICE probe obtained was used as a hybridization probe on a human genomic DNA.

The human genomic DNA was prepared from peripheral blood mononuclear cells (PBMC) with the TurboGen kit (Invitrogen) then cleaved by the restriction enzymes BglII, PstI, HindIII or BamHI (Boehringer Mannheim) respectively, migrated on a 0.9% agarose gel in 1× TAE, transferred onto a nylon GeneScreen Plus membrane (NEN Dupont) then hybridized with the exon 6 ICE probe.

The hybridization conditions are those described by Maniatis et al. (already quoted) carried out in 5×SSPE, 10×Denhart, 100 μg/ml DNAss, 1% SDS, overnight at 65° C. followed by washings carried out successively in 2×SSC, 0.05% SDS, 30 mn at ambient temperature then 1×SSC, 0.1% SDS, 30 mn at 65° C., which corresponds to high stringency. The washing buffer is prepared from the following stock solutions. 20×SSC: 3 M aqueous solution of sodium chloride, 0.3 M sodium citrate.

10% SDS: aqueous solution of sodium dodecyl sulphate,

After washing, the membrane is exposed with a Hyperfilm-MP film (Amersham).

Figure 1:
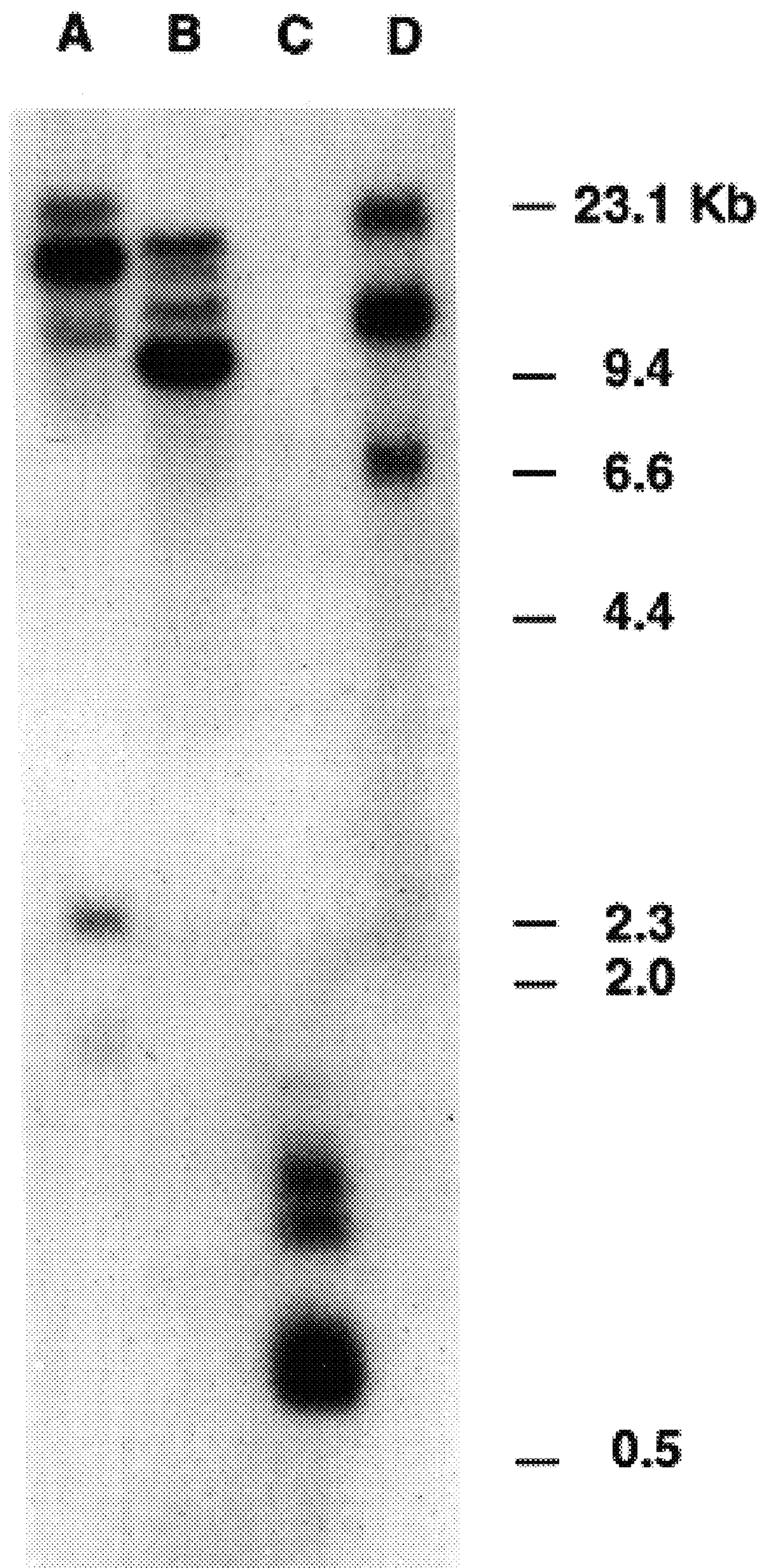
FIG. 1 represents the detection of sequences homologous to ICE by Southern Blot in human genomic DNA originating from PBMC digested by the restriction enzymes BglII (line A); PstI (line B); HindIII (line C); BamH1 (line D). The detection is carried out by hybridization with an ICE exon 6 probe labelled with $^{32}$P.

As is shown in FIG. 1, for each of the restriction enzymes three to four different bands are observed corresponding to DNA fragments of different size which probably, for certain of them, correspond to genes which are highly homologous to ICE but different from the latter since a single gene can only produce one or at most two distinct bands during a hybridization with a probe corresponding to a single exon.

B—Cloning of Genes Homologous to ICE a) Cloning of Genomic Sequences Homologous to ICE In order to identify the different fragments of DNA obtained above, the fragments of human genomic DNA extracted from peripheral blood mononuclear cells (PBMC) then digested by the HindIII enzyme (Boehringer Mannheim) were separated by preparative electrophoresis in 1.5% agarose gel, 1×TAE, according to the conditions described by Maniatis et al. (already quoted). The gel was cut into 20 fractions in the area corresponding to the molecular weights which are lower than 2.3 kb then amplification using PCR was carried out on the DNA eluted from each of the fractions using oligonucleotides ICE 6.5 (SEQ ID NO: 3) and ICE 6.3 (SEQ ID NO: 4) described above, using the following amplification conditions: 94° C., 1 mn; 55° C., 1 mn; 72° C., 1 mn; 30 cycles; BioTaq polymerase.

Among the above 20 fractions, eight fractions having produced the best amplification using PCR were retained. The amplified material was cloned using the T4-DNA ligase enzyme in the vector pCRII according to the supplier's instructions with the TA Cloning kit (Invitrogen) and sequenced by the Sanger technique with the Sequenase enzyme using the Macrophor electrophoresis equipment (Pharmacia System). The sequences determined were analyzed by means of GCG software (Devereux et al. Nucleic Acids Research 12, 387–395 (1984)).

Among the nucleotide sequences obtained, we have identified a sequence called T2 which has a 92% identity of nucleotides with the sequence of exon 6 of ICE.

The nucleotide sequence T2 has an open reading frame over all of the exon 6 (SEQ ID NO: 5) represented in FIG. 2, which leads to an attempt to identify the messenger RNA's coding for a protein T2 and to clone the cDNA corresponding to T2.

b) Cloning of the cDNA Homologous to ICE

The total RNA's were extracted and purified using a RNA™ kit (Bioprobe) starting with either monocytes activated by LPS for 18 hours, or placenta, or polynuclear cells isolated from peripheral blood. Each corresponding cDNA was synthesized using a poly-dT oligonucleotide and the reverse transcriptase enzyme using the GeneAmp RNA PCR Kit (Perkin Elmer) according to the supplier's instructions then amplified using PCR using the following two oligonucleotides:

T2.A: CTACAGAGCTGGAGGCATTTGCT (SEQ ID NO: 6)

chosen from the sequence coding for exon 6 of T2, so as to specifically amplify a sequence of T2 type but not an ICE sequence, and

ICE45.3 TTAATGTCCTGGGAAGAGGTAGAA (SEQ ID NO: 7)

chosen from the 3' end of the coding region of the cDNA of ICE (complementary strand).

A fragment of approximately 600 base pairs was obtained respectively from each of the 3 RNA preparations using the following amplification conditions: 94° C., 30 s; 60° C., 30 s; 72° C., 30 s; 30 cycles with the GeneAmp RNA PCR Kit (Perkin Elmer). The fragment was cloned using the TA Cloning kit (Invitrogen) and sequenced as indicated above. The nucleotide sequence thus determined does not correspond to an expected T2 cDNA but to a new cDNA which we have called Tx.

C—Identification of the Tx cDNA a) Determination of the Consensus Sequence of Tx cDNA The nucleotide sequences of the 5' and 3' ends of the cDNA of Tx were obtained by the anchored PCR technique from a cDNA of the placenta.

The 5' end of the cDNA of Tx was amplified using the 5'-Race-Ready cDNA kit (Human Quick-Clone cDNA) (Clontech) and the following amplification oligonucleotides:

TxPCR5A: GAGGCAGTTG CGGTTGTTGA A (SEQ ID NO: 8)

TxPCR5B: CTCTGACCCA CAGTTCCCCA C (SEQ ID NO: 9)

The 3' end of the Tx cDNA was amplified using the 3' RACE System kit (Gibco-BRL), and the following amplification oligonucleotides:

TxA: AACTGTGCAT GATGAGA (SEQ ID NO: 10)

TxB: AGATGCTGTG TACAAGACC (SEQ ID NO: 11)

These two respective pairs of primers were defined from the partial sequence of Tx obtained above.

The amplification fragments obtained were then cloned using the TA Cloning kit (Invitrogen) and sequenced as indicated above.

The nucleotide sequences were confirmed thanks to the use of the TxA oligonucleotides (SEQ ID NO: 10) and TxB oligonucleotides (SEQ ID NO: 11) above and the following oligonucleotides:

TxC: GCCTGGACAA TGATGAC (SEQ ID NO: 12)

TxD: TGATGAAGAT AGAGCCC (SEQ ID NO: 13)

Tx1: CGGGTCATGG CAGACTC (SEQ ID NO: 14)

Tx2: GTTTGAAGAA GCATTTG (SEQ ID NO: 15)

Tx3: CCTGAGTCAG GAGAATC (SEQ ID NO: 16)

Tx4: AGTCTCAGGA ATTCTTC (SEQ ID NO: 17)

Tx5: AGCTGACTTT GACATCA (SEQ ID NO: 18)

Tx6: GCGCTGACTC CATATCC (SEQ ID NO: 19)

which were chosen from the sequence coding for Tx (coding strand or complementary strand).

The compilation of all of the sequences obtained produces the consensus nucleotide sequence of the Tx cDNA (SEQ ID NO: 1) represented in FIG. 3. The sequence thus determined comprises 1291 nucleotides ending with a polyadenylation sequence. It has an open reading frame beginning with a methionine initiator at nucleotide 42 and ending with a termination codon at nucleotide 1172. The result is an open reading frame of 1131 nucleotides coding for a protein of 377 amino acids.

b—Cloning of the Coding Region of the Tx cDNA

The coding region of the Tx cDNA (SEQ ID NO: 1) was amplified by RT-PCR from the total RNA either of monocytes, or of polynuclear cells or of placenta using the following oligonucleotides:

TxP5: CGCGGATCCACCATGGCAGAAGGCAA CCACAGA (SEQ ID NO: 20)

TxP3: GGCTCTAGACTCGAGTTATCAATTGC-CAGGAAAGAGGTA (SEQ ID NO: 21)

These amplification primers were chosen according to the Tx cDNA consensus sequence previously determined (or the complementary strand) and synthesized by adding BamH1 and Nco1 cloning sites for the oligonucleotide TxP5 and Xba1 and Xho1 cloning sites for the oligonucleotide TxP3 respectively.

The amplified product obtained having a length of approximately 1150 base pairs was digested by the enzymes BamH1 and Xba1 (Boehringer Mannheim) and cloned, by using the Amersham ligation kit, in the vector pcDNAI/Amp (Invitrogen) digested beforehand by the same restriction enzymes BamH1 and Xba1. The cloned product was entirely sequenced over the two strands, by means of the oligonucleotides TxA, TxB, TxC, TxD, Tx1, Tx2, Tx3, Tx4, Tx5 and Tx6 above.

For each starting RNA used, the nucleotide sequence obtained is identical to the sequence coding for the Tx cDNA consensus sequence (SEQ ID NO: 1) above. Therefore no difference is observed between the different tissues used which originate from different individuals.

The coding region of the Tx cDNA codes for the protein Tx the derived amino acid sequence of which (SEQ ID NO: 2) is shown in FIG. 3. The sequence of the protein Tx includes 377 amino acids having a calculated molecular weight of 43.26 kDa.

The homology of the sequence of the protein Tx with the precursor ICE p45 is at most 52% identicalin terms of amino acids by introducing discontinuities in the alignment of the sequences.

A sample of *E. coli* XL-1 blue containing the region coding for the Tx cDNA (SEQ ID NO: 1) in the vector pcDNAI/Amp (Tx cDNA/pcDNAI 13/07/94) was deposited at the CNCM on Jul. 29, 1994 under the number I-1462.

c—Expression of the Tx mRNA in Various Human Tissues

The expression of the mRNA coding for the protein Tx was studied in eight different tissues by Northern Blot using a DNA probe corresponding to the part of Tx which is aligned with exon 6 of ICE ("Tx exon 6"). This probe corresponds to nucleotides 595 to 811 of the sequence SEQ ID NO: 1.

The probe "Tx exon 6" was prepared by amplifying this sequence starting from the plasmid containing the Tx cDNA using as primers the oligonucleotides T2.A (SEQ ID NO: 6) and TxC (SEQ ID NO: 12) above.

This probe was labelled with $^{32}P$ by the method of random priming with the Oligolabelling kit (Pharmacia BioTech) then used to detect by hybridization the Tx mRNA's on a membrane containing 2 $\mu g$ of RNA polyA+ respectively of different human tissues on a Multiple Tissue Northern Blot II membrane (Clontech) according to the hybridization conditions provided by the supplier.

Figure 4:
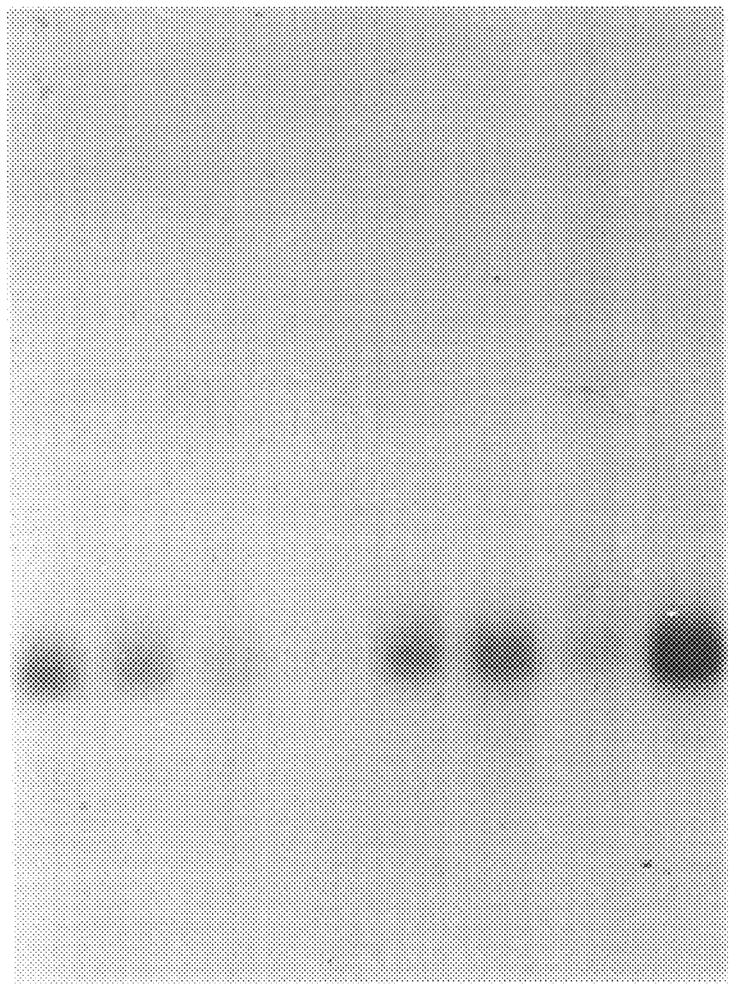
FIG. 4 represents the detection of Tx mRNA by Northern Blot in tissues of the spleen (line A); the thymus (line B); the prostate (line C); the testicle (line D); the ovary (line E); the small intestine (line F); the colon (line G); the peripheral leucocytes (line H). The detection is carried out by hybridization with a "Tx exon 6" probe labelled with $^{32}$P.

As is shown in FIG. 4, an mRNA signal is detected in most of the tissues tested with variable intensities. The peripheral blood leucocytes (H) produce the strongest signal. The spleen (A), the small intestine (F), the thymus (B) and the ovary (E) produce intermediate signals. The prostate (C) and the colon (G) produce a very weak signal and finally no signal is detected in testicle mRNA (D).

The mRNA coding for the protein Tx is therefore expressed in many tissues and quite particularly in blood cells.

EXAMPLE 2

Study of the Function of the Protein Tx

A—Cleavage of the Pre-IL-1β

The capacity of the protein Tx to optionally cleave the precursor of human IL-1β was tested in a eukaryotic cell transfection system with one or other of the expression vectors pcDNAI/Amp and pcDL-SRalpha296.

The region coding for the Tx cDNA (SEQ ID NO: 1) was first cloned at the BamH1 and Xba1 sites of the eukaryotic expression vector pcDNAI/Amp (Invitrogen). After digestion with the enzymes BamH1 and Xba1, an insert of about 1150 base pairs was isolated then purified. The restriction sites of the ends were filled using T4 DNA Polymerase (Boehringer Mannheim). The cDNA obtained was subcloned using a ligation kit (Amersham) in the vector pcDL-SRalpha296 (Takebe et al., Molecular and Cellular Biology, Vol. 8, 466, 1988) opened by the Xba1 enzyme then the ends of which were filled by T4 DNA Polymerase. After purification using the plasmid maxi kit (QIAGEN), Tx plasmid DNA preparations in the two vectors were obtained.

The eukaryotic cells used for the transfection are a Cos-1 cell line which constitutively expresses pIL-1β and which was obtained by transfection of a plasmid containing the gene of human pIL-1β. The synthesis of pIL-1β is maintained in this line by cultivating the cells in the presence of 0.5 mg/ml of G-418 sulphate in a DMEM, 10% FCS, glutamine, P/S, pyruvate, HEPES culture medium.

$3\times10^6$ Cos-1 cells are incubated at 37° C. in a humid atmosphere with 5% $CO_2$ in Petri dishes and transfected by 15 μg of plasmid DNA previously mixed with 200 μl of DEAE-DEXTRAN and diluted with 4 ml of PBS before being added to the dishes. After incubation of the cells at 37° C. for 30 minutes and the addition of 8 ml of an 80 μM chloroquine solution in DMEM without serum, the cells are incubated for 2.5 hours. The supernatant solution is then aspirated and the cells are treated for two minutes with DMSO at 10% in DMEM without serum. After washing with the medium without serum, 10 ml of the above complete culture medium is added. After incubation, the supernatant of the transfected cells is collected at different times comprised between 16 and 45 hours.

The mature IL-1β present in the supernatants is measured using an ELISA IL1-β test (R&D Systems) which allows the specific detection of mature IL-1β.

The transfection was carried out with the coding region of the Tx cDNA inserted in one or other of the two vectors above in comparison with transfections containing the coding region of the cDNA of ICE p45 or ICE p30 respectively as well as a control transfection with the corresponding vector alone not containing plasmid.

Figure 5A:
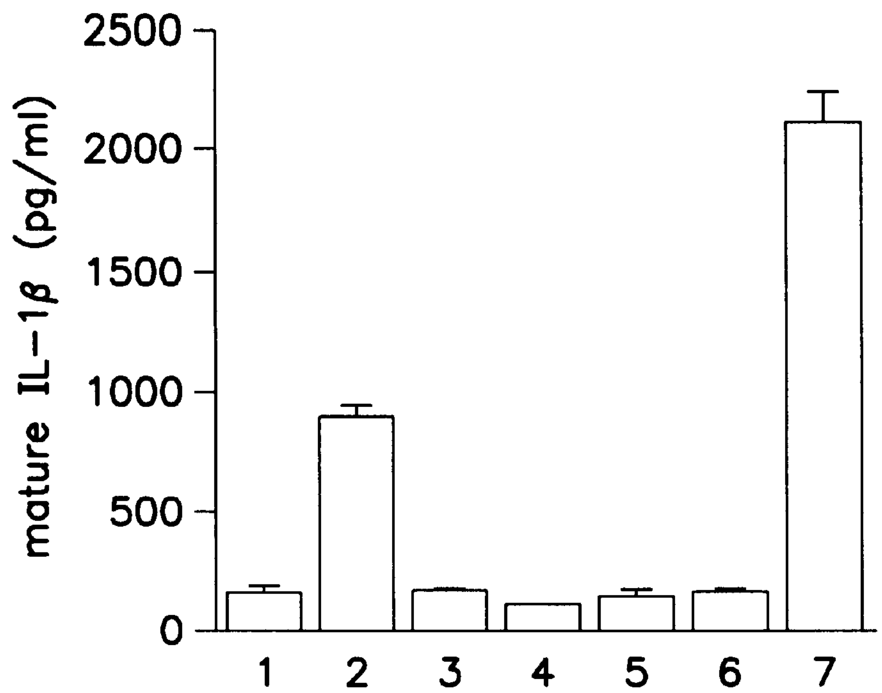
FIGS. 5A and B represents the secretion of mature IL-1β in Cos-1 cells containing constitutively pIL-1β and transfected by the vector pcDL-SRalpha296 containing ICE p45 (line 2) or Tx (line 3), the vector pcDL-SRalpha296 alone (line 4), the vector pcDNAI/Amp alone (line 5), the vector pcDNAI/Amp containing Tx (line 6) or ICE p30 (line 7) compared to a control culture without DNA (line 1). The mature IL-1β is measured in pg/ml of cellular supernatant using ELISA (A: incubation for 16 hours; B: incubation for 24 hours).
Figure 5B:
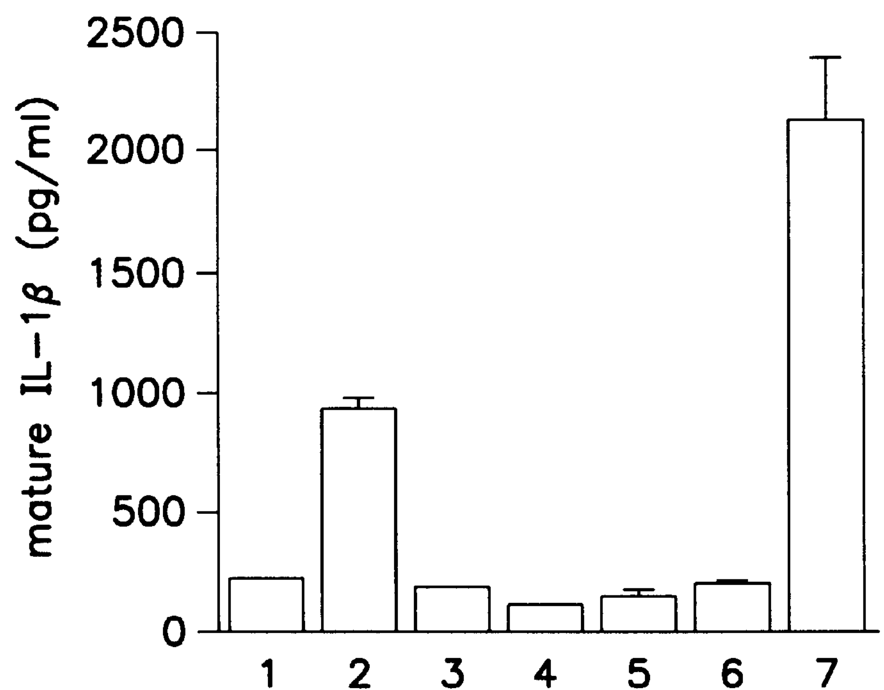

As is shown in FIG. 5, the transfection of the cDNA of ICE p45 (column 2) or p30 (column 7) confers on the cells the capacity to secrete mature IL-1β. By contrast, when the Tx cDNA is transfected under the same conditions (columns 3 and 6), no secretion of IL-1β is observed as for the control transfections (columns 1, 4, 5). Similar results are obtained with the two expression vectors whatever the incubation time (16 h: FIG. 5A; 24 h: FIG. 5B; 29 h and up to 44 h) after the transfection.

The protein Tx does not possess the convertase property of IL-1β.

B—Protease Activity of the Protein Tx: Cleavage of the 30 kDa Precursor of ICE

The capacity of the protein Tx to optionally cleave the 30 kDa precursor of ICE (ICE p30) was tested in a co-transfection system in eukaryotic cells by simultaneously introducing into Cos-1 cells a vector containing the coding region of the Tx cDNA (SEQ ID NO: 1) and a vector containing a DNA coding for a modified ICE protein, each DNA being respectively inserted into the expression vector pcDL-SRalpha296 above.

The protein ICE was doubly modified: On the one hand, to allow a specific detection of the protein ICE in the presence of the protein Tx, a small T7 peptide was fused to the N terminal end of the protein ICE p30. The protein thus marked or its maturation products are detectable by Western Blotting with a monoclonal antibody specific to the T7 peptide (Tsai et al., Proc. Natl. Acad. Sci., 89, 8864, 1992). On the other hand to express the enzyme in a form which is incapable of inducing its own maturation, a mutant of ICE p30 was used, the cysteine Cys 285 of the active site of which was replaced by a serine (Wilson, K. P. et al. Nature, 370, Jul. 28, 1994, 270–275). This enzyme is thus inactive and incapable of inducing its own maturation or cleaving pIL-1β. The mutant was prepared by site-directed mutagenesis using the appropriate oligonucleotides and the Transformer™ site-directed mutagenesis kit (Clontech). The sequence obtained was entirely verified. In this way the marked and mutated ICE p30 is obtained designated T7-ICEp30C285S.

Cos-1 cells were transfected either with the vector pcDL-SRalpha296 containing T7-ICEp30C285S, or with the vector pcDL-SRalpha296 container Tx or co-transfected with the two vectors, following the above operating conditions. After culture for 22 hours, the cells were collected, washed and lysed in a buffer containing 10 mM NaCl, 10 mM Hepes, pH 7.4, 1 mM EDTA, 50 mM NaF, 0.2% Triton X-100, 1 μg/ml leupeptin, 20 u/μl aprotinin and 1 mM PMSF. The cellular lysate was centrifuged at 400 g and 4° C. then the supernatant was subjected to an electrophoresis on a 16% polyacrylamide gel using SDS-PAGE. The proteins of the gel were then transferred onto a nitrocellulose membrane and incubated with the anti-T7 mouse monoclonal antibody (Novagen) for 2 hours at ambient temperature. The membrane was washed then incubated for 1 hour at ambient temperature with a mouse anti-immunoglobulin goat antibody conjugated with alkaline phosphatase. The antibodies fixed to the membrane are then revealed by the alkaline phosphatase substrate (Promega).

Co-transfections were carried out in the same manner with the vector pcDL-SRalpha296 containing T7-ICEp30C285S and the vector pcDL-SRalpha296 containing either ICE p30, or ICE p45 in place of Tx.

Figure 6:
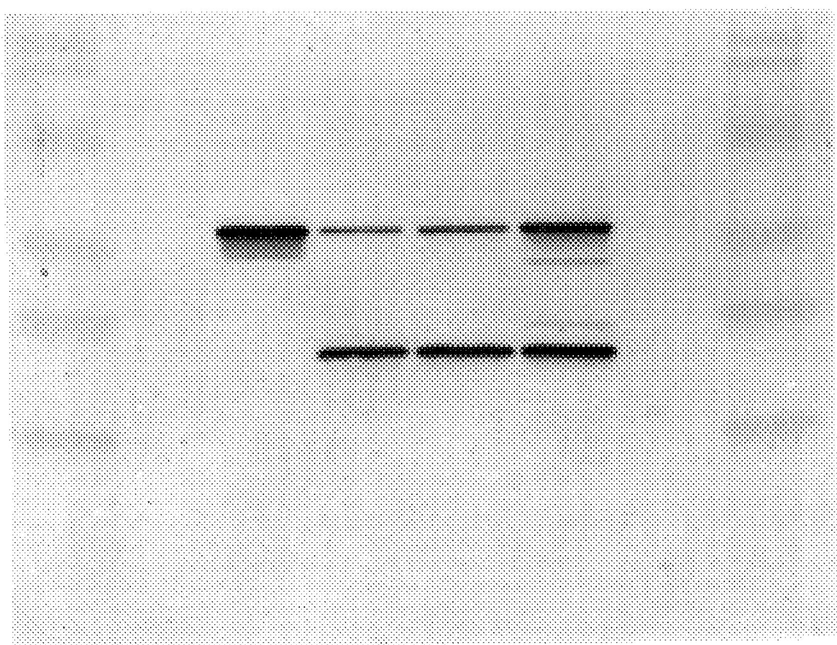
FIG. 6 represents the cleavage of the precursor ICE p30 in Cos-1 cells transfected by the vector pcDL-SRalpha296 alone (line A) or containing the labelled mutant T7-ICEp30C285S (line B) or co-transfected with the vector pcDL-SRalpha296 containing the labelled mutant T7-ICEp30C285S and the vector containing ICE p30 (line C) or ICE p45 (line D) or Tx (line E). The detection is carried out using Western Blot with the anti-T7 antibody with a control corresponding to a transfection by the vector pcDL-SRalpha296 containing Tx alone (line F).
Figure 7A:
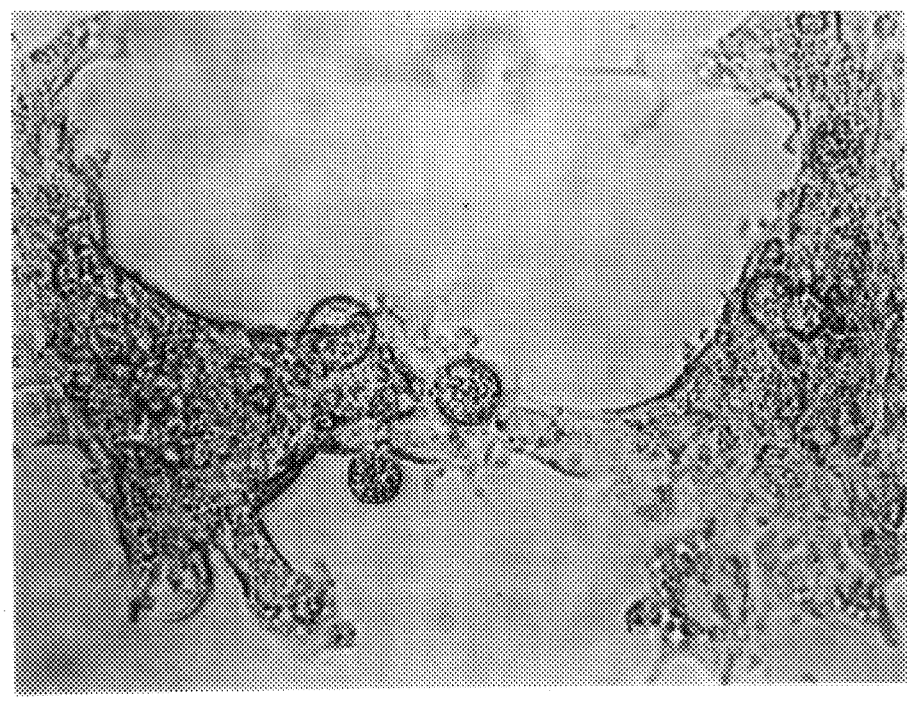
FIGS. 7A–D represents the induction of apoptosis by the protein Tx in Cos-1 cells transfected by the vector pcDL-SRalpha296 alone (7B) or containing Tx (7C) or ICE p45 (7D) compared to a control culture without DNA (7A) after culture for 22 hours (magnification×400).
Figure 7B:
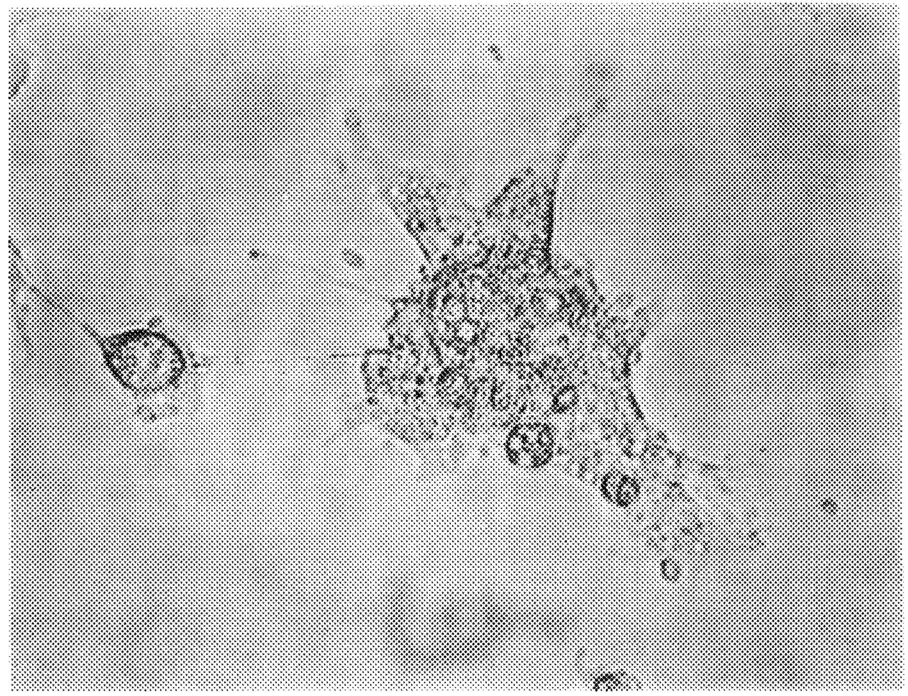
Figure 7C:
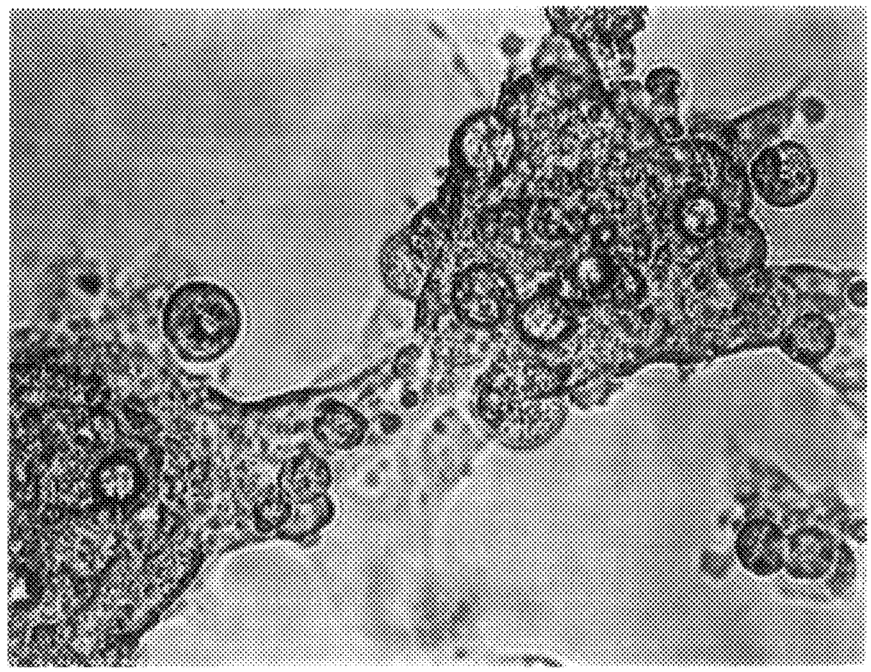
Figure 7D:
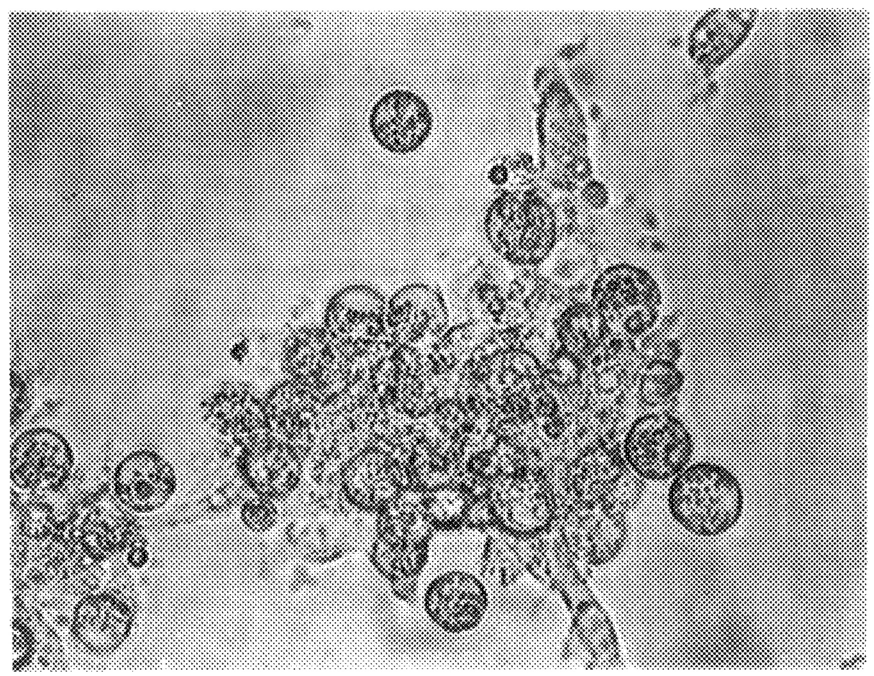

As is shown in FIG. 6, when the mutated protein ICE p30 (T7-ICEp30C285S) is expressed alone in the transfected Cos cells, the T7-p30 form of the enzyme (apparent MW 35 kDa) can be detected (line B).

The absence of a band corresponding to the p20 form shows that the mutated enzyme is incapable of self-cleavage. When the cells are co-transfected by the vector containing the ICE p30 enzyme (line C) or the p45 enzyme (line D), a band is observed at an apparent MW of 26 kDa corresponding to the cleavage product of T7-p20 by the active enzyme. When the cells are co-transfected by the vector containing Tx (line E), the appearance of a major band is also observed at an apparent MW of 26 kDa accompanied by two minor bands of approximately 31 kDa and 28 kDa. The different bands correspond to the cleavage products of the p30 form of the ICE by the protein Tx expressed in the cells.

These results show that the protein Tx, on the one hand is expressed in the transfected Cos cells, and on the other hand has a protease activity. In addition, the protein Tx is capable of cleaving the 30 KDa precursor of ICE and can thus contribute to the maturation in vivo of the pro-enzyme of ICE and to the generation of the enzyme in active form.

C—Induction of Apoptosis by the Protein Tx

The capacity of the protein Tx to induce apoptosis was tested by transfection in Cos cells and by morphological examination of the cultured cells.

The transfection of ICE in different cell types leading to the death of these cells by apoptosis has been described (Miura et al. already quoted).

The transfection of Cos-1 cells by the vector pcDL-SRalpha296 containing the coding region of the Tx cDNA (SEQ ID NO: 1) as well as transfection with the vector pcDL-SRalpha296 containing ICE p45 was carried out as described above. The morphology of the cells was observed after an incubation of 22 hours.

As is shown in FIG. 7, the appearance of round cells is observed which detach themselves from the support and the morphological appearance of which is characteristic of cells in apoptosis in the Cos cell cultures transfected by the cDNA of ICE (7D). The same change in morphology is observed in Cos cell cultures transfected by Tx cDNA (7C).

Identical morphological results were obtained when the above vector pcDNAI/Amp is used to express ICE and Tx in transfected Cos-1 cells.

These results were confirmed by observation of the DNA isolated from transfected Cos-1 cells and incubated 40 hours after transfection. The DNA of the cells was prepared with the microTurboGen kit (Invitrogen), migrated on 1.5% agarose gel and stained with BET.

Figure 8:
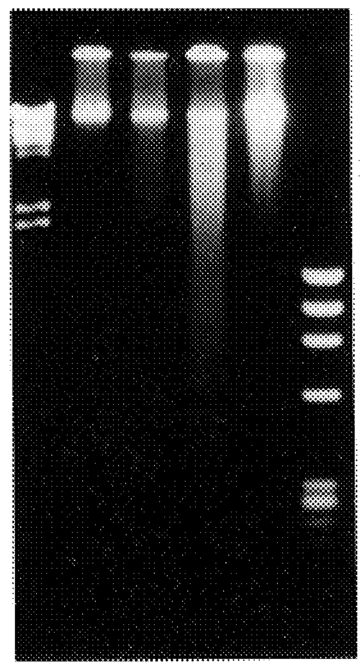
FIG. 8 represents the DNA of Cos-1 cells transfected by the vector pcDL-SRalpha296 containing ICE p45 (line B) or Tx (line C) or by the vector alone (line D) compared to a control culture without DNA (line A). The detection is carried out by staining with BET after migration on an agarose gel with DNA size markers of the lambda phage digested by HindIII (M1) and DNA of phage φX174 digested by HindIII (M2).

As shown in FIG. 8, the DNA of the cells transfected with ICE p45 (line B) and with Tx (line C) have the characteristic "scalariform" appearance of cells in apoptosis.

Cells transfected without DNA (7A and 8A) or with the vector not containing cDNA (7B and 8D) have neither the morphology nor the DNA of cells in apoptosis.

These results show that the protein Tx is involved in the induction of apoptosis.

EXAMPLE 3

Identification of the Ty Sequence

A—Cloning of Genes Homologous to Tx

The human genomic DNA extracted from peripheral blood mononuclear cells was digested by the Hind III enzyme (Boehringer Mannheim), then the fragments were separated by preparative electrophoresis in 1% agarose, 1×TAE gel, according to the conditions described by Maniatis et al., already quoted. The gel was cut into 24 fractions in the area of the deposition wells corresponding to molecular weights greater than 1.9 kb then amplification using PCR was carried out on the DNA eluted from each of the fractions using the T2A (SEQ ID NO: 6) and TxC (SEQ ID NO: 12) oligonucleotides already described and using the following amplification conditions: 94° C., 30 sec.; 55° C., 30 sec.; 72° C., 1 mn; 30 cycles; BioTaq polymerase (BioProbe).

Among the above 24 fractions, 10 fractions which produced the best amplification using PCR were retained. The amplified material was purified on agarose gel and was cloned in the vector PCRII with the TA Cloning kit (Invitrogen) and sequenced by the Sanger technique with the Sequenase enzyme (Version 2.0 DNA Sequencing Kit) using the Macrophor electrophoresis system (Pharmacia System). The determined sequences were analyzed by means of GCG software as indicated in Example 1.

A nucleotide sequence was identified called Ty which has a 94.9% identity in terms of nucleotides with the Tx cDNA sequence (SEQ ID NO: 1) and which leads an attempt to clone the cDNA corresponding to Ty.

B—Cloning and Identification of Ty cDNA a) Determination of the Consensus Sequence of Ty cDNA The nucleotide sequences of the 5' and 3' ends of the cDNA of Ty were obtained from the cDNA of human spleen and placenta respectively using the anchored PCR technique.

The 3' end of the cDNA of Ty was amplified using the 3'RACE System kit (Gibco-BRL), and the following amplification oligonucleotides:

Ty 3.2: CATGTCTCATGGCATCCTA (SEQ ID NO: 24)

and

Ty 3.1: CTGCGGAACTGCGCATAAAA (SEQ ID NO: 25).

These two primers were defined from the partial sequence of the exon 6 of the Ty sequence obtained above. The amplified fragments were purified on agarose gel, cloned in the vector pCRII and sequenced as indicated above. Compilation of the sequences obtained allowed the 3' part of the coding region of the Ty cDNA as well as the non-coding 3' region to be defined.

The 5' end of the cDNA of Ty was been amplified using the Human Spleen 5'-RACE-Ready cDNA kit (Clontech) and the following amplification oligonucleotides:

Ty5A1: GGCTCTAGACTCGAGGTGCTCT TTGATGTTGACAG (SEQ ID NO: 26)

and

Ty5A4: CTTCTCCTCGTGGATCTTGC (SEQ ID NO: 27).

These two primers were defined from the sequence of the 3' region of the Ty cDNA obtained above by adding the restriction sites Xba1 and Xho1 for Ty5A1. The amplification fragments were then cloned using the TA Cloning kit (Invitrogen) and sequenced as indicated above.

The nucleotide sequences were confirmed by using the Ty5A1 (SEQ ID NO: 26) and Ty 3.1 (SEQ ID NO: 25) oligonucleotides above and the following oligonucleotides:

Ty 2: AGATGTTCTTCATGGT (SEQ ID NO: 28)

Ty 4: CTTCTCAATATGGACCA (SEQ ID NO: 29)

Ty 5: CCTGGCTCTCATCATAT (SEQ ID NO: 30)

Ty 6: ATTTGCTGCCAGACCAGA (SEQ ID NO: 31)

Ty 7: GCCTGCAGAGGTGAAAAAC (SEQ ID NO: 32)

Ty 8: GCTCCATCTTCATTACGGA (SEQ ID NO: 33)

Ty 0: GATTTCTGTACCTTCCG (SEQ ID NO: 34)

Ty A: TTTATGCGCAGTTCCG (SEQ ID NO: 35)

Ty B: GTCATAGTGAGCCCCATT (SEQ ID NO: 36)

Ty C: CTTCACGAGGACAAAGT (SEQ ID NO: 37)

Ty D: TCGCAAAGAGTCTACCA (SEQ ID NO: 38)

These oligonucleotides were chosen from the coding sequence of Ty (coding strand or complementary strand).

Compilation of all the sequences obtained produces the consensus nucleotide sequence of the Ty cDNA (SEQ ID NO: 22).

b) Cloning of the Coding Region of Ty cDNA

The coding region of the Ty cDNA (SEQ ID NO: 22) was amplified using PCR starting from the cDNA of human spleen or placenta using the corresponding 5'-RACE-Ready cDNA kit (Clontech), the oligonucleotide Ty5A1 (SEQ ID NO: 26) above and the following oligonucleotide:

TyP5: CGCGGATCCAAGATGTTGGAATA CCTGGGCAAA (SEQ ID NO: 39).

These amplification primers were chosen according to the consensus sequence of the Ty cDNA (SEQ ID NO: 22) determined above by adding the cloning site BamH1 for TyP5.

The product which had been amplified and purified on agarose gel and having a length of approximately 1100 base pairs was digested by the restriction enzymes BamH1 and Xba1 then cloned in the vector pcDNAI/Amp as described in Example 1 and sequenced as indicated above. The cloned product was entirely sequenced over the two strands using the oligonucleotides SEQ ID NO: 28 to SEQ ID NO: 38 defined above.

An identical sequence to the coding sequence of the consensus sequence Ty cDNA (SEQ ID NO: 22) was obtained. The homology of the coding sequence of the Ty cDNA with the codign sequence of the Tx cDNA obtained in Example 1 is 84% identity of nucleotides.

The coding region of the Ty cDNA codes for the Ty protein having the derived amino acid sequence SEQ ID NO: 23. The protein sequence contains 364 amino acids having a calculated molecular weight of 41.8 kDa.

The homology of sequence of the Ty protein with the Tx protein obtained in Example 1 is 75% identity of amino acids.

A sample of *E. coli* XL-1 blue containing the coding region of the Ty cDNA (SEQ ID NO: 22) in the vector PcDNAI/Amp (Ty cDNA/pcDNAI/Amp 30/6/95) was deposited at the CNCM on Jul. 5, 1995 under the No. I-1068.

EXAMPLE 4

Biological Activities of the Protein Ty

A—Induction of Apoptosis

The capacity of the protein Ty to induce apoptosis was tested according to the operating method indicated in Example 2, using Cos-1 cells transfected by the vector pcDL-SRalpha296 containing the coding region of the Ty cDNA (SEQ ID NO: 22) named pcDL-TY, and the preparation of which was carried out according to the conditions described in Example 2 for the sub-cloning of the Tx cDNA.

The morphology of the cells was observed after incubation for 23 hours and 43 hours and observation of the isolated DNA was carried out after incubation for 43 hours.

The results, obtained in comparison to cells transfected by the vector containing the coding region of Tx or ICE p45, are identical to those shown for the protein Tx in FIG. 7 and in FIG. 8 of Example 2.

These results show that the protein Ty as well as the protein Tx is involved in the induction of apoptosis.

B—Protease Activity of the Protein Ty

The capacity of the protein Ty to self-cleave in an intermolecular manner was tested in a co-transfection system in eukaryotic cells, under similar conditions to those to described for cleavage of the precursor of ICE by the protein Tx in Example 2, by simultaneously introducing into Cos-1 cells a vector containing the coding region of the Ty cDNA (SEQ ID NO: 22) and a vector containing a DNA coding for a modified protein Ty, each DNA being inserted in the expression vector pcDL-SRalpha296 and in the vector pcDNAI/Amp described in Example 2 respectively.

The protein Ty was doubly modified, on the one hand the Cys 245 codon was mutated into a Serine codon by the "overlapping" PCR method, on the other hand the epitope tag T7 (MASMTGGQQMG) was introduced into the N-terminal end of the Ty fragment corresponding to residues 68 to 364 of the sequence SEQ ID NO: 23.

The following pairs of primers were used to amplify the TY cDNA template:

a) on the one hand,

T7TY: CGCGGATCCACCATGGCTTCTATGACAG-GAGGTCAACAAATGGGACAAAAGATCACCAGTG TAAAACC (SEQ ID NO: 40)

chosen from the coding sequence of Ty and synthesized by adding a restriction site BamH1 followed by the nucleotide sequence coding for tag T7 and

TYC245SR: ATGTTTTTCACCTCTGGAGGCCTGGA-CAATGATGAC (SEQ ID NO: 41)

chosen from the coding sequence of Ty (complementary strand) with a C→G mutation in position 17, b) on the other hand,

TYC245S: GTCATCATTGTCCAGGCCTCCAGAGGT-GAAAAACAT (SEQ ID NO: 42)

chosen from the coding sequence of Ty with a G→C mutation in position 20 and Ty5A1 (SEQ ID NO: 26) above, and using the following amplification conditions: 94° C., 1 mn; 60° C., 1 mn; 72° C., 1 mn; 30 cycles; Vent polymerase (Biolabs). The two amplification products obtained respectively were combined and amplified by PCR by using primers T7Ty and Ty5A1 and the above conditions.

The amplification product was digested with the restriction enzymes BamH1 and Xba1 then cloned in the vector pcDNAI/Amp digested beforehand by the same restriction enzymes. The resulting plasmid is called pT7TYΔ67C245S. The sequence obtained was entirely verified by DNA sequencing.

The expression vector pcDL-SRalpha296 in which the Ty cDNA sequence (SEQ ID NO: 22) was sub-cloned, called plasmid pcDL-TY, was prepared as indicated above.

Cos-1 cells were either transfected by the vector pT7TYΔ67C245S, or co-transfected with this plasmid and the plasmid pcDL-TY then cultured for 23 hours or 43 hours, lysed and analyzed by electrophoresis on polyacrylamide gel and Western blot using the mouse anti-T7 monoclonal antibody, according to the operating conditions described in Example 2, but in which the mouse anti-immunoglobulin goat antibody is conjugated to horseradish peroxidase instead of the alkaline phosphatase. The antibodies linked to the membrane are then revealed with the ECL Western detection system (Amersham) using autoradiography.

Co-transfections were carried out in the same manner with the vector pcDL-SRalpha296 alone and the vector pcDNAI/Amp and the cells were cultured for 23 hours.

Figure 9:
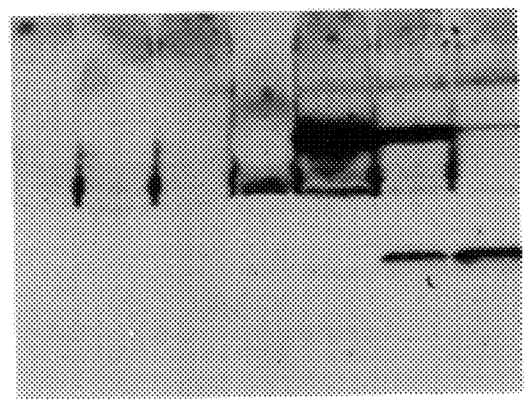
FIG. 9 represents the cleavage of the mutated protein Ty (T7TYΔ67C245S) in Cos-1 cells, either transfected by the vector pcDL-SRalpha296 alone (line B) or the vector pcDNAI/Amp alone (line C) or the vector pT7TYΔ67C245S (line E), or co-transfected by the vector pT7TY and the vector pT7TYΔ67C245S (line F; 23 hours and line G; 43 hours). The detection is carried out by Western Blot compared to a control culture without DNA (line A) and molecular weight markers (line D; non-detectable).

As shown in FIG. 9, when the mutated protein Ty is expressed alone in transfected Cos cells, the T7Ty form (apparent MW approximately 30 kDa) can be detected (line E). The absence of a band of lower MW shows that the mutated protein Ty is incapable of self-cleaving. When the cells are co-transfected with the vector containing Ty (lines F and G), the appearance of a major band is observed at an apparent MW of 20 kDa corresponding to the cleavage product of the protein Ty mutated by the protein Ty.

These results show that the protein Ty is on the one hand expressed in transfected Cos cells, and on the other hand has a protease activity and that it is in particular capable of self-cleaving in an intermolecular manner.

We claim:

1. An isolated DNA molecule consisting of SEQ ID No: 22 encoding a polypeptide having a protease activity and capable of inducing apoptosis.

2. A method of producing a polypeptide consisting of SEQ ID No: 23 comprising culturing cells transformed by a vector containing the DNA molecule of SEQ ID No: 22 of claim 1.

* * * * *